United States Patent

Ito

[11] Patent Number: 5,837,720
[45] Date of Patent: Nov. 17, 1998

[54] N-2-(PYRROLIDINYL-1)-1-PHENETHYL) ACETAMIDES AS KAPPA RECEPTOR ANTAGONISTS

[75] Inventor: Fumitaka Ito, Chita-gun, Japan

[73] Assignee: Pfizer Inc., New York, N.Y.

[21] Appl. No.: 793,225

[22] PCT Filed: May 18, 1995

[86] PCT No.: PCT/IB95/00374

§ 371 Date: Apr. 17, 1997

§ 102(e) Date: Apr. 17, 1997

[87] PCT Pub. No.: WO96/06077

PCT Pub. Date: Feb. 29, 1996

[51] Int. Cl.$^6$ .......... A61K 31/40; C07D 207/12; C07C 233/13; C07C 233/31
[52] U.S. Cl. .......... 514/343; 514/364; 514/408; 514/422; 514/428; 546/276.4; 548/131; 548/143; 548/517; 548/527; 548/568; 564/162; 564/163; 564/169; 564/182; 564/193; 564/199; 564/210
[58] Field of Search .......... 514/343, 364, 514/408, 422, 428; 546/276.4; 548/131, 143, 517, 527, 568

[56] References Cited

U.S. PATENT DOCUMENTS 5,232,978  8/1993  Gottschlich et al. .......... 514/422

FOREIGN PATENT DOCUMENTS 0483580  5/1992  European Pat. Off. .
0569802  11/1993  European Pat. Off. .

OTHER PUBLICATIONS

"2–(3,4–Dichlorophenyl)–N–methyl–N–[2–(1–pyrolidinyl)–1–substitued–ethyl]–acetamides:The Use of Conformational Analysis in the Development of a Novel Series of Potent Opioid k Agonists," Costello et al., *J. Med. Chem.* 1991 (Jan.), 34(1), 181–189.

"Structure/Activity Studies Related to 2–(3,4–Dichlorophenyl)–N–methyl–N–[2–(1–pyrrolidinyl)–substituted–ethyl] acetamides:A Novel Series of Potent and Selective k–Opioid Agonists," Barlow et al., *J. Med. Chem.* 1991 (Nov.), 34(11), 3149–3158.

*Primary Examiner*—Johann Richter
*Assistant Examiner*—Jane C. Oswecki
*Attorney, Agent, or Firm*—Peter C. Richardson; Paul H. Ginsburg

[57] ABSTRACT

A compound of formula (I):

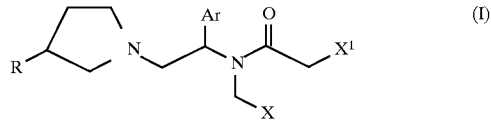

and its pharmaceutically acceptable salt, wherein R is hydrogen or hydroxy; Ar is unsubstituted or substituted phenyl; X is unsubstituted or substituted phenyl or heterocyclic, mono-, di- or trihalomethyl, cyano, or the like; and $X^2$ is phenyl, naphthyl, furyl, thienyl, pyridyl, thiazolyl, benzofuryl or benzothienyl, each of which may either be unsubstituted or substituted. These compounds have agonist activity toward opioid kappa receptors and are thus useful as analgesic, anti-inflammatory, diuretic and neuroprotective agents.

11 Claims, No Drawings

N-2-(PYRROLIDINYL-1)-1-PHENETHYL) ACETAMIDES AS KAPPA RECEPTOR ANTAGONISTS

This application is a 371 of PCT/IB95/00374 filed May 18, 1995.

TECHNICAL FIELD

This invention relates to novel carboxamide compounds and their pharmaceutically acceptable salts, and to pharmaceutical compositions containing them. These compounds and compositions are useful as analgesic, antiinflammatory, diuretic or neuroprotective agents for the treatment of a mammalian subject, especially a human subject.

BACKGROUND ART

Opioid analgesics such as morphine are therapeutically useful, but their usage is strictly limited because of their side effects such as drug dependency. Thus, analgesics with high usefulness and reduced tendency to cause drug dependency are desired. Considerable pharmacological and biochemical studies have been carried out to discover the opioid peptides and opioid receptors, and the discovery of the subtype of opioid receptor such as mu, delta, kappa at a peripheral nerve in a variety of species, including human, has made a beginning towards creating new analgesics. As it is thought that opioid analgesics such as morphine act as a $\mu$-receptor agonist, separating the action based on a kappa-receptor agonist from the action based on $\mu$-receptor agonist has been investigated. Recently kappa-selective agonists have been reported from the above viewpoint for example, EMD-60400: A. Barber et al., Naunyn-Schmled. Arch. Pharmacol., 345 (Suppl.): Abst 456. Some of them actually have been studied in clinical trials (Med. Res. Rev., 12, 525 (1992)).

However, even when a selective kappa-receptor agonist is employed, use of high doses can give rise to side effects such as sedation. Therefore, it would be desired to provide compounds having better agonist activity toward opioid kappa receptor.

BRIEF DISCLOSURE OF THE INVENTION

The present invention provides a compound of the following formula:

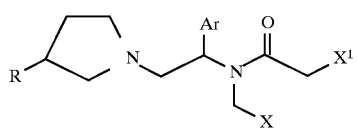

and its pharmaceutically acceptable salt, wherein

R is hydrogen or hydroxy;

Ar is phenyl or phenyl substituted with one to three substituents selected from halo, $C_{1-4}$ alkyl and $C_{1-4}$ alkoxy;

X is phenyl or heterocyclic; phenyl or heterocyclic substituted with one to three substituents selected from halo, $C_{1-4}$ alkyl, $C_{1-4}$ alkoxy and methoxycarbonyl; mono-, di- or tri-halomethyl; cyano; $COR^1$, $CH=NOR^2$, $OR^2$, $SR^2$, $CH_2CN$, $CH_2OR^2$, $CH_2SR^2$, $CH_2S(O)R^2$, $CH_2S(O)_2R^2$, $CH_2(R^2)R^3$, $CH_2N(R^2)R^3$, $CH_2NR^2OH$, $CH_2N(COR^2)OH$, $CH_2NR^2COR^3$, $CH_2NR^2S(O)_2R^3$ or $CH_2OCOR^2$, wherein $R^1$ is hydrogen, hydroxy, amino, NHOH, $NHOCH_3$, pyridylamino, $NHN(CH_3)_2$, $C_{1-4}$ alkoxy, benzyloxy, $C_{1-4}$ alkylamino, di-$C_{1-4}$ alkylamino, $C_{1-4}$ alkyl or $C_{1-4}$ alkylthio; and $R^2$ and $R^3$ are each hydrogen, $C_{1-4}$ alkyl, $C_{1-4}$ alkoxy or $C_{7-11}$ phenylalkyl; and $X^1$ is phenyl, naphtyl, furyl, thienyl, pyridyl, thiazolyl, benzofuryl or benzothienyl; phenyl, naphtyl, furyl, thienyl, pyridyl, thiazolyl, benzofuryl or benzothienyl, substituted with one to three substituents selected from halo, $C_{1-4}$ alkyl, $C_{1-4}$ alkoxy, amino, hydroxy, nitro, trifluoromethyl and mesyl.

Further, the present invention provides a compound of the formula:

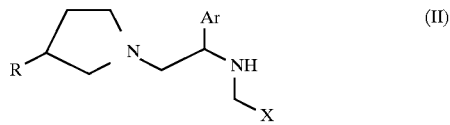

wherein R, Ar and X are as already defined. These compounds can be used as intermediates to prepare the compounds of formula (I).

The carboxamide compounds of the present invention of formula (I) exhibit significant agonist activity toward opioid kappa receptor and are thus useful as analgesic, antiinflammatory, diuretic and neuroprotective agents, in mammals, especially man.

Accordingly, the present invention also provides a pharmaceutical composition useful as an analgesic, antiinflammatory, diuretic or neuroprotective agent, in a mammal, especially man, which comprises a therapeutically effective amount of the carboxamide compound of formula (I) or its pharmaceutically acceptable salt together with a pharmaceutically acceptable carrier.

DETAILED DISCLOSURE OF THE INVENTION

In this specification, the term "heterocyclic" means a monocyclic or bicyclic hydrocarbon group which has one or more hetero atoms in the ring, preferably has 4 to 10 carbon atoms and 1 to 3 heteroatoms, including piperidino, morpholino, thiamorpholino, pyrrolidino, pyrazolino, pyrazolidino, pyrazoryl, piperazinyl, furyl, benzofuryl, thienyl, benzothienyl, oxazolyl, tetrazolyl, thiazolyl, imidazolyl, pyrazolyl, pyridyl, pyrimidinyl, pyrrolyl, pyrrolidinyl, quinolyl and quinuclidinyl.

A preferred group of compounds of this invention includes the compounds of formula (I) wherein R is hydroxy; Ar is phenyl optionally substituted with one to three halogen atoms, preferably phenyl; X is phenyl optionally substituted with one to three substituents selected from halo, $C_{1-4}$ alkyl, $C_{1-4}$ alkoxy and methoxycarbonyl; and $X^1$ is phenyl optionally substituted with one to three halogen atoms, preferably 3,4-dichlorophenyl.

Another preferred group of compounds of this invention includes the compounds of formula (I) wherein R is hydroxy; Ar is phenyl optionally substituted with one to three halogen atoms, more preferably phenyl; X is mono-, di- or tri-halomethyl, cyano, hydroxycarbonyl, butyloxycarbonyl, benzyloxycarbonyl, carbamoyl or hydroxymethyl; and $X^1$ is phenyl optionally substituted with one to three halogen atoms, preferably 3,4-dichlorophenyl.

Another preferred group of compounds of this invention includes the compounds of formula (I) wherein R is hydroxy; Ar is phenyl optionally substituted with one to three halogen atoms, more preferably phenyl; X is furyl, thienyl, pyridyl or oxadiazolyl; and $X^1$ is phenyl optionally substituted with one to three halogen atoms, preferably 3,4-dichlorophenyl.

Preferred individual compounds of the invention are:

N-carboxymethyl-2-(3,4-dichlorophenyl)-N-[2-(3-(S)-hydroxypyrrolidin-1-yl)-1-(S)-phenylethyl]acetamide;

2-(3,4-dichlorophenyl)-N-(2-hydroxyethyl)-N-[2-(3-(S)-hydroxypyrrolidin-1-yl)-1-(S)-phenylethyl]acetamide;

2-(3,4-dichlorophenyl)-N-[(2-(3-(S)-hydroxypyrrolidin-1-yl)-1-(S)-phenylethyl]-N-(2,2,2-trifluoroethyl)acetamide;

2-(3,4-dichlorophenyl)-N-furfuryl-N-[2-(3-(S)-hydroxypyrrolidin-1-yl)-1-(S)-phenylethyl]acetamide;

2-(3,4-dichlorophenyl)-N-[2-(3-(s)-hydroxypyrrolidin-1-yl)-1-(s)-phenylethyl]-N-(4-pyridyl)methylacetamide;

2-(3,4-dichlorophenyl)-N-[2-(3-(S)-hydroxypyrrolidin-1-yl)-1-(S)-phenylethyl]-N-(3-pyridyl)methylacetamide;

N-cyanomethyl-2-(3,4-dichlorophenyl)-N-[2-(3-(S)-hydroxypyrrolidin-1-yl)-1-(S)-phenylethyl]acetamide;

2-(3,4-dichlorophenyl)-N-(2,2-difluoroethyl)-N-[2-(3-(S)-hydroxypyrrolidin-1-yl)-1-(S)-phenylethyl]acetamide;

N-2-cyanoethyl-2-(3,4-dichlorophenyl)-N-[2-(3-(S)-hydroxypyrrolidin-1-yl)-1-(S)-phenylethyl]acetamide;

2-(3,4-dichlorophenyl)-N-[2-(3-(S)-hydroxypyrrolidin-1-yl)-1-(S)-phenylethyl]-N-methoxycarbonylmethylacetamide; and 2-(3,4-dichlorophenyl)-N-[2-(3-(S)-hydroxypyrrolidin-1-yl)-1-(S)-phenylethyl]-N-(1,2,4-oxadiazol-3-yl)methylacetamide.

General Synthesis

The carboxaimde compounds of formula (I) of this invention may be prepared by a variety of synthetic methods. For example, the carboxamide compounds of formula (I) may be prepared by acylation of compound (II), as indicated in the following Preparation Method A-I.

Preparation Method A-I:

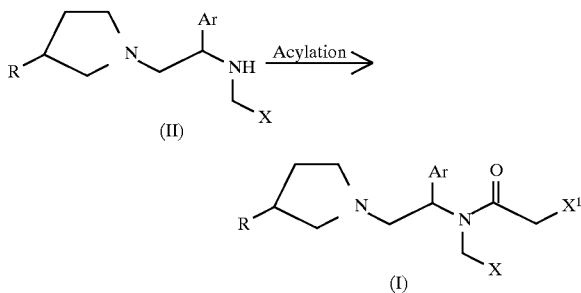

(wherein R, Ar, X and $X^1$ are as previously defined)

In Preparation Method A-I, the amine compound (II) is reacted with an acylating agent using standard acylating techniques known to those skilled in the art. In a typical acylation method, the amine compound (II) may be reacted with acyl halide (e.g., $X^1CH_2COCl$) in a suitable reaction-inert solvent. Suitable inert-reaction solvents include, for example, aromatic hydrocarbons such as benzene, toluene and xylene; ethers such as ethyl ether, dioxane and tetrahydrofuran; halogenated hydrocarbons such as chloroform, dichloromethane and dichloroethane; amides such as N,N-dimethylformamide; and nitriles such as acetonitrile. If desired, this reaction may be catalyzed by a base such as triethylamine, pyridine or alkoxide. The reaction may be carried out at a temperature of from –30° C. to 100° C., preferably from 0° C. to 25° C., for 10 minutes to 48 hours, preferably 30 minutes to 24 hours.

The compound (I) of the present invention may also be obtained from the amine compound (II) by the other acylation methods, for example, (1) a reaction with anhydride (e.g., $(X^1CH_2CO)_2O$) or a mixed anhydride in the presence of base; (2) a reaction with carboxylic acid ($X^1CH_2COOH$) in the presence of a coupling agent such as dicyclohexyl-carbodiimide (DCC), water soluble carbodiimide (WSCD), 2-ethoxy-N-ethoxycarbonyl-1,2-dihydroquinoline, Bop agent (Benzotriazol-1-yloxy-tris(dimethylamino) phosphonium hexafluorophosphate), diethyl azodicarboxylate-triphenylphosphine, diethyl cyanophosphonate, carbonyldiimidazole and diphenylphospholyl azide; or (3) a reaction with carboxylic ester (e.g., $X^1CH_2COOR'$ wherein R' is lower alkyl) optionally in the presence of base. The conditions employed for the acylation methods can be properly chosen by the skilled persons.

In an alternative method, the compound (I) of the present invention may be prepared by the following Preparation Method A-II.

Preparation Method A-II:

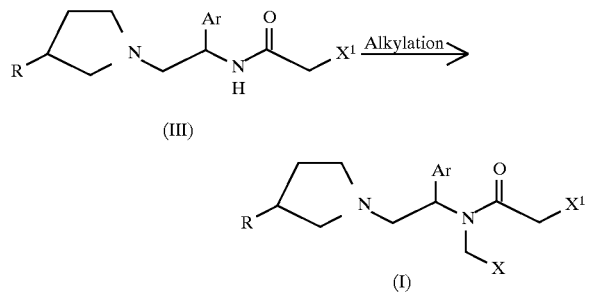

In this method, the compound (I) may be obtained by alkylation of the amide compound (III). Alkylation methods known to those skilled in the art can be used. For example, the amide compound (III) may be reacted with alkylhalide (e.g., $XCH_2L$ wherein X is as previously defined; and L is halo such as chloro) in a reaction-inert solvent. If desired, this reaction may be catalyzed by a base such as sodium, sodium hydride, sodium hydroxide, potassium hydroxide, with or without a phase-transfer catalyst. The reaction may be carried out at a temperature of from 0° C. to 200° C., preferably from 60° C. to 150° C., for 5 minutes to 24 hours, preferably from 30 minutes to 12 hours.

Alternatively, the alkylation of the compound (III) may be carried out by reacting the compound (III) with formaldehyde and metal salts (e.g., MX wherein X is as previously defined; and M is an alkali metal such as sodium and potassium) in a suitable reaction-inert solvent. In addition, the amide compound (III) may be obtained by acylation of the amine compound (IV) in similar procedures to those described in Preparation Method A-I above.

In the present invention, the amine compound (II) may be obtained by the following Preparation Method B-I.

Preparation Method B-I:

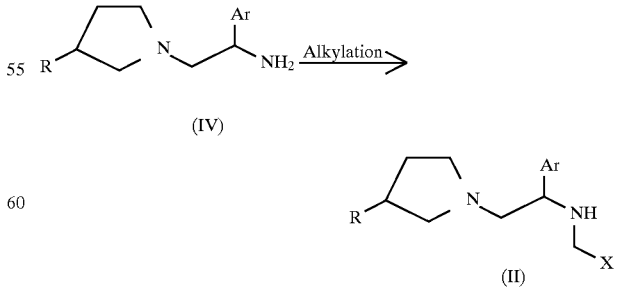

In this method, the amine compound (II) may be obtained by alkylation of the amine compound (IV) using standard alkylation techniques known to those skilled in the art. A preferred alkylation method is reductive alkylation wherein the amine compound (IV) may be reacted with aldehyde, XCHO (wherein X is as already defined) in the presence of a reducing agent such as $NaBH_4$, $NaBH_3CN$ or $NaBH(OAc)_3$. This reaction may be carried out in a suitable reaction-inert solvent at a temperature of from $-20°$ C. to $60°$ C., preferably from $0°$ C. to $25°$ C., for 10 minutes to 48 hours, preferably from 60 minutes to 5 hours. In an alternative alkylation method, the amine compound (II) may be obtained by reacting the amine compound (IV) with alkylhalide, $XCH_2L$ (wherein X and L are as already defined) under conditions known to those skilled in the art. The Mannich type alkylation can be also used, which comprises the reaction of the compound (IV) with formaldehyde and a metal salt. The amine compounds (IV) are either known or may be prepared by known methods as described in European Patent No. 254545.

Alternatively, the amine compound (II) may be obtained by acylation of the compound (IV), followed by reduction, as indicated in the following Preparation Method B-II.

Preparation Method B-II:

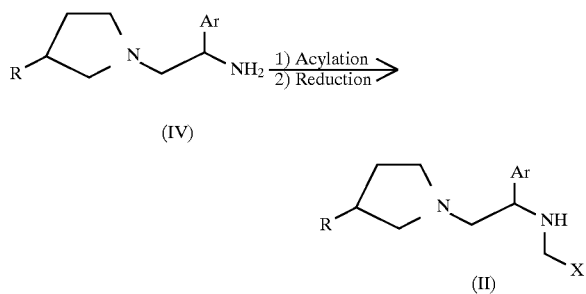

In a typical procedure, the amine compound (IV) may be first reacted with acylating agents, XCOOH (wherein X is as already defined) in the presence of a suitable coupling agent as mentioned above, in a suitable reaction-inert solvent, followed by reduction using a reducing agent such as $LiAlH_4$, $BH_3.Me_2S$ or $BH_3.THF$. This reaction may be carried out at a temperature of from $0°$ C. to $100°$ C., preferably from $20°$ C. to $80°$ C., for 30 minutes to 24 hours, preferably from 60 minutes to 12 hours. The other possible acylation methods prior to the reduction include a reaction of the compound (IV) with acyl halide, XCOL in the presence of base; and the reaction of the compound (IV) with anhydride, $(XCO)_2O$ in the presence of base. The conditions to be employed for these acylation methods can be appropriately chosen by those skilled in the art.

Further, the compound (II) may be obtained by acylation of an amide compound of the following formula (V), followed by reduction, as indicated in the following Preparation Method B-III.

Preparation Method B-III:

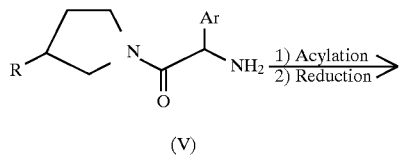

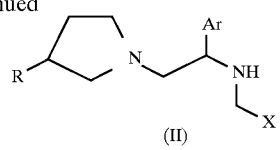

In this method, the amide compound (V) may be first subjected to acylation as mentioned in the above Preparation Method B-II, and then subjected to reduction, to obtain the compound (II). The conditions for this reaction may be similar to those described in the above Preparation Method B-II. In addition, the amide compound (V) is either known or can be prepared by known methods as described in, for example, European Patent No. 254545 and Chem. Pharm. Bull., 42(3) 690–693, 1994.

The compounds of formula (I), and the intermediates shown in the above Preparation Methods can be isolated and purified by conventional procedures, such as recrystallisation or chromatographic purification.

As the carboxamide compounds of this invention possess at least two asymmetric centers, they are capable of occurring in various stereoisomeric forms or configurations. Hence, the compounds can exist in separated (+)- and (−)-optically active forms, as well as mixtures thereof. The present invention includes all such forms within its scope. Individual isomers can be obtained by known methods, such as optically selective reaction or chromatographic separation in the preparation of the final product or its intermediate.

The carboxamide compounds of the present invention can be used in the form of the inorganic salts with acid such as hydrochloric acid, hydrobromic acid, sulfonic acid, nitric acid, phosphoric acid and the like and the organic salts with acid such as acetic acid, formic acid, benzoic acid, oxalic acid, succinic acid, fumaric acid, maleic acid, citric acid, alkylsulfonic acid.

The carboxamide compounds of the present invention of formula (I) exhibit significant agonist activity toward opioid kappa receptor and are thus useful as analgesic, antiinflammatory, diuretic and neuroprotective agents for the treatment of mammals, especially humans in need of such agents.

The activity of the carboxamide compounds of formula (I) of the present invention as opioid kappa agonist, is demonstrated by the opioid receptor binding activity. Such activity may be determined in homogenates from guinea pig whole brain, as described by Regina, A. et al. in J. Receptor Res. 12: 171–180, 1992. In summary, tissue homogenate is incubated at $25°$ C. for 30 min in the presence of labelled ligand and test compounds. The $\mu$-sites are labelled by 1 nM of (3H)-[D-Ala2,MePhe4,Gly-ol5]enkephalin (DAMGO), the δ-sites by 1 nM of (3H)-[D-Pen2,5]enkephalin (DPDPE) and the κ-sites by 0.5 nM (3H)-CI-977. The non specific binding is measured by use of 1 mM CI-977 (κ), 1 mM (DAMGO) ($\mu$), 1 mM (DPDPE) (δ). Data are expressed as the $IC_{50}$ values obtained by a non-linear fitting program using the Cheng and Prusoff equation. All compounds prepared in the Working Examples as described below were tested by this method, and showed an $IC_{50}$ value of 0.01 nM to 10 $\mu$M with respect to inhibition of binding at its receptor.

The agonist activity toward opioid kappa receptor can also be demonstrated by the Formalin Test as described by Wheeler-Aceto, H. et al. in Psychopharmacology 104: 35–44, 1991. In this testing, male SD rats (80–100 g) are injected s.c. with a test compound dissolved in 0.1% methyl cellulose saline or vehicle. After 30 min., 50 ml of a 2% formalin are injected into a hind paw. The number of licking the injected paw per observation period is measured 15–30 min. after the injection of formalin and expressed as % inhibition compared to the respective vehicle group.

The agonist activity toward opioid kappa receptor can also be demonstrated by the Rotarod Test as described by Hayes, A. G. et al. in Br. J. Pharmacol. 79: 731–736, 1983. In this testing, a group of 6–10 male SD rats (100–120 g) are selected for their ability to balance on a rotating rod (diameter 9 cm, rate of rotation 5 r.p.m.). The selected rats are then injected s.c. with a test compound dissolved in 0.1% methyl cellulose saline. The animals are tested again 30 min. after treatment; a rat falling off the bar more than twice within 150 seconds is considered to be showing motor impairment and the animal's performance (i.e., time on the rotarod) are recorded. The $ED_{50}$ value, defined as the dose of the drug which halves the performance time is observed in the control group.

The carboxamide compounds of formula (I) of this invention can be administered via either the oral, parenteral or topical routes to mammals. In general, these compounds are most desirably administered to humans in doses ranging from 0.01 mg to 100 mg per day, although variations will necessarily occur depending upon the weight and condition of the subject being treated, the disease state being treated and the particular route of administration chosen. However, a dosage level that is in the range of from 0.01 mg to 50 mg per kg of body weight per day is most desirably employed for the treatment of pain in a postoperative patient.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral-pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene grycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES

The present invention is illustrated by the following examples. However, it should be understood that the invention is not limited to the specific details of these examples. Melting points were taken with a Buchi micro melting point apparatus and uncorrected. Infrared Ray absorption spectra (IR) were measured by a Shimazu infrared spectrometer (IR-470). $^1$H and $^{13}$C nuclear magnetic resonance spectra (NMR) were measured in $CDCl_3$ by a JEOL NMR spectrometer (JNM-GX270, 270 MHz) unless otherwise indicated and peak positions are expressed in parts per million (ppm) downfield from tetramethylsilane. The peak shapes are denoted as follows: s, singlet; d, doublet; t, triplet; m, multiplet; br, broad.

Preparation 1
(S)-Phenylglycyl-3-(S)-hydroxypyrrolidine

To a stirred solution of 3-(S)-pyrrolidinol (3.054 g, 35 mmol) and N-benzyloxycarbonyl-(S)-phenylglycine (10.00 g, 35 mmol) in DMF (40 ml) was added diethyl phosphorocyanidate (6.28 ml, 42 mmol) followed by addition of N-methylmorpholine (4.65 ml, 42 mmol) at room temperature.

After 1 h stirring at room temperature, the reaction mixture was poured into water (200 ml), extracted with mixed solvent (ethyl acetate/hexane/ether: 2/1/1, 100 ml×3). The extract combined was washed with 1N HCl solution, saturated $NaHCO_3$ aqueous solution and brine, dried ($MgSO_4$), and concentrated to give 11.395 g (91.9%) of N-benzyloxycarbonyl-(S)-phenylglycyl-3-(S)-hydroxypyrrolidine as yellow oil. A suspension mixture of this oil (11.395 g, 32 mmol) and 10% palladium carbon (1.14 g) in methanol (100 ml) was stirred under hydrogen atmosphere at room temperature for 17 h. The catalyst was removed by Celite filtration and the filtrate was concentrated to give 8.255 g (crude 100%) of the title compound as brown oil.

$^1$H NMR (270 MHz, $CDCl_3$) δ 7.45–7.27 (5H, m), 4.56 (0.7H, s), 4.49 (0.3H, s), 4.45–4.35 (1H, m), 3.74–3.36 (3H, m), 3.25–3.15 (0.7H, m), 3.10–2.98 (0.3H, m), 2.70 (2H, br.s), 2.30 (1H, br.s), 2.05–1.75 (2H, m).

IR (neat): 3350, 3300, 1640 $cm^{-1}$.

To a stirred solution of 3-(S)-pyrrolidinol (14.70 g, 169 mmol) and N-t-butoxycarbonyl-(S)-phenylglycine (42.46 g, 169 mmol) in DMF (250 ml) was added diethyl phosphorocyanidate (30.3 ml, 203 mmol) followed by addition of N-methylmorpholine (22.5 ml, 203 mmol) at room temperature. After 1 h stirring at room temperature, the reaction mixture was poured into water (1250 ml), extracted with mixed solvent (ethyl acetate/hexane/ether:2/1/1, 400 ml×3).

The extract combined was washed with 1N HCl solution, saturated NaHCO$_3$ aqueous solution and brine, dried (MgSO$_4$), and concentrated to give 34.81 g (64.3%) of N-t-butoxycarbonyl-(S)-phenylglycyl-3-(S)-hydroxypyrrolidine as white powder. To a stirred suspension of N-t-butoxycarbonyl-(S)-phenylglycyl-3-(S)-hydroxypyrrolidine (10.13 g, 31.6 mmol) in CH$_2$Cl$_2$ (10 ml) was added trifluoroacetic acid (25 ml) at 0° C. and resulting solution was stirred at room temperature for 1 h. After evaporation of excess trifluoroacetic acid and solvent, the residue was basified with aqueous NH$_3$ solution (20 ml) and extracted with CH$_2$Cl$_2$ (30 ml×3). After dry (Na$_2$SO$_4$), the solvent was evaporated to give 4.974 g (71.5%) of title compound.

Preparation 2
(2S,3S)-1-(2-Amino-2-phenylethyl)-3-hydroxypyrrolidine

To a stirred suspension of lithium aluminum hydride (3.795 g, 100 mmol) in THF (200 ml) was added a solution of (S)-phenylglycyl-3-(S)-hydroxypyrrolidine (7.049 g, 32 mmol) in THF (100 ml) dropwise at room temperature. The reaction mixture was refluxed for 1.5 h. Then the reaction mixture was cooled down to room temperature and Na$_2$SO$_4$.10H$_2$O (10.31 g) and KF (1.86 g) was added to the reaction mixture. After 1 h stirring, the white solid precipitated was removed by Celite filtration and the filtrate was concentrated to give 4.21 g of clear yellow oil. This was purified by column chromatography (silica gel: 180 g, CH$_2$Cl$_2$/MeOH/NH$_4$OH: 50/5/1 as eluent) to afford 3.584 g (54.3%) of clear yellow oil.

$^1$H NMR (270 MHz, CDCl$_3$) δ 7.38–7.15 (5H, m), 4.37–4.29 (1H, m), 4.08 (1H, dd, J=4.0, 10.3Hz), 3.08–3.01 (1H, m), 2.77 (1H, dd, J=10.3, 12.1 Hz), 2.69–2.61 (1H, m), 2.43 (1H, dd, J=4.0, 12.1Hz), 2.31–2.00 (6H, m), 1.83–1.70 (1H, m).

IR (neat): 3350, 3200 cm$^{-1}$.

Preparation 3
(2S,3S)-1-[2-N-(Benzyloxycarbonyl)methylamino-2-phenylethyl]-3-hydroxypyrrolidine A mixture of (2S,3S)-1-(2-amino-2-phenylethyl)-3-hydroxypyrrolidine (1.65 g, 8 mmol), benzyl 2-bromoacetate (1.52 ml, 9.6 mmol), and triethylamine (1.34 ml, 9.6 mmol) in CH$_2$Cl$_2$ (30 ml) was refluxed for 7 h. The reaction mixture was diluted with water (50 ml), then extracted with CH$_2$Cl$_2$ (50 ml×3). The extract combined was washed with brine and dried (MgSO$_4$). Evaporation of the solvent gave 2.18 g of brown oil which was purified by column chromatography (silica gel:70 g, CH$_2$Cl$_2$/MeOH: 20/1 to 10/1 as eluent) to afford 1.218 g (42.9%) of clear yellow oil.

$^1$H NMR (270 MHz, CDCl$_3$) δ 7.40–7.22 (10H, m), 5.13 (2H, s), 4.35–4.25 (1H, m), 3.82 (1H, dd, J=3.7, 11.0Hz), 3.43 (1H, d, J=17.6Hz), 3.22 (1H, d, J=17.6Hz), 3.16–3.06 (1H, m), 2.86 (1H, dd, J=11.0, 12.1Hz), 2.70 (1H, dd, J=4.8, 10.3Hz), 2.64 (1H, dd, J=1.8, 9.9Hz), 2.31 (1H, dd, J=3.7, 12.1Hz), 2.26–2.15 (4H, m), 1.82–1.71 (1H, m).

IR (neat): 3350, 1740 cm$^{-1}$.

Example 1
N-(Benzyloxycarbonyl)methyl-2-(3,4-dichlorophenyl)-N-[2-(3-(S)-hydroxypyrrolidin-1-yl)-1-(S)-phenylethyl]acetamide To a stirred solution of (2S,3S)-1-[2-N-(benzyloxycarbonyl)methylamino-2-phenylethyl]-3-hydroxypyrrolidine (354 g, 1 mmol) in dioxane (4 ml) was added 1N NaOH aqueous solution (1 ml) followed by dropwise addition of 3,4-dichlorophenylacetyl chloride at room temperature. After 2.5 h stirring, the reaction mixture was extracted with CH$_2$Cl$_2$. The extract combined was washed with brine, dried (MgSO$_4$), and concentrated to give 0.952 g of brown viscous oil, which was purified by column chromatography (silica gel: 30 g, CH$_2$Cl$_2$/MeOH: 30/1 to 10/1 as eluent) to afford 152 mg (28.1%) of title compound as yellow brown viscous oil.

$^1$H NMR (270 MHz, CDCl$_3$) δ 7.39–7.27 (11H, m), 7.15–7.08 (1.5H, m), 7.01 (0.5H, dd, J=2.2, 8.4Hz), 6.04 (0.5H, dd, J=5.9, 9.9Hz), 5.10 (1H, s), 5.07 (0.5H, d, J=12.1Hz), 5.00 (0.5H, t, J=7.5Hz), 4.99 (0.5H, d, J=12.1Hz), 4.28 (0.5H, d, J=16.8Hz), 4.30–4.20 (1H, m), 3.97 (0.5H, d, J=18.7Hz), 3.92 (0.5H, d, J=16.5Hz), 3.89 (0.5H, d, J=15.7Hz), 3.76 (1H, s), 3.71 (0.5H, d, J=16.1Hz), 3.60 (0.5H, d, J=15.7Hz), 3.14–2.42 (5H, m), 2.27–2.01 (2H, m), 1.80–1.60 (2H, m).

IR (neat): 3450, 1750, 1650 cm$^{-1}$.

This oil was converted to HCl salt using HCl gas saturated methanol to give 77 mg of amorphous solid.

Anal. Calcd for C$_{29}$H$_{30}$Cl$_2$N$_2$O$_4$.HCl.1.5H$_2$O: C, 57.58; 5.66; N, 4.63 Cl, 17.58. Found: C, 57.56; H, 5.37; N, 4.71; Cl, 17.67.

Example 2
(2S,3S)-1-[2-N-(t-Butoxycarbonyl)methylamino-2-phenylethyl]-3-hydroxypyrrolidine This compound was prepared in 70% yield according to a procedure similar to that described in Preparation 3.

$^1$H NMR (270 MHz, CDCl$_3$) δ 7.34–7.28 (5H, m), 4.38–4.30 (1H, m), 3.81 (1H, dd, J=3.7, 10.6Hz), 3.25 (1H, d, J=17.6Hz), 3.19–3.13 (1H, m), 3.04 (1H, d, J=17.6Hz), 2.87 (1H, dd, J=10.6, 12.1Hz), 2.75–2.65 (2H, m), 2.34 (1H, dd, J=3.7, 11.7Hz), 2.27–2.15 (4H, m), 1.85–1.75 (1H, m), 1.44 (9H, s).

IR (neat) 3300, 1730 cm$^{-1}$.

Example 3
N-(t-Butoxycarbonyl)methyl-2-(3,4-dichlorophenyl)-N-[2-(3-(S)-hydroxypyrrolidin-1-yl)-1-(S)-phenylethyl] acetamide This compound was prepared in 37.1% yield according to a procedure similar to that described in Example 1.

$^1$H NMR (270 MHz, CDCl$_3$) δ 7.41–7.10 (8H, m), 6.10 (0.7H, dd, J=6.6, 9.6Hz), 5.03 (0.3H, dd, J=7.0, 7.7Hz), 4.30–4.20 (1H, m), 3.93 (0.3H, d, J=16.8Hz), 3.82 (0.6H, s), 3.82 (0.7H, d, J=18.7Hz), 3.76 (0.3H, d, J=15.4Hz), 3.71 (0.7H, d, J=18.7Hz), 3.62 (0.7H, d, J=15.8Hz), 3.55 (0.7H, d, J=15.8Hz), 3.17–2.05 (9H, m), 1.80–1.65 (1H, m), 1.39 (2.7H, s), 1.30 (6.3H, s).

IR (neat): 3400, 1740, 1650 cm$^{-1}$.

Anal. Calcd for C$_{26}$H$_{32}$Cl$_2$N$_2$O$_4$.0.5H$_2$O: C, 60.47; H, 6.44; N,5.42. Found: C, 60.24; H, 6.41; N, 5.24.

Example 4
N-Carboxymethyl-2-(3,4-dichlorophenyl)-N-[2-(3-(S)-hydroxypyrrolidin-1-yl)-1-(S)-phenylethyl]acetamide A mixture of N-(t-butoxycarbonyl)methyl-2-(3,4-dichlorophenyl)-N-[2-(3-(S)-hydroxypyrrolidin-1-yl)-1-(S)-phenylethyl]acetamide (306 mg, 0.6 mmol), HCl gas saturated methanol solution (8 ml), and methanol (2 ml) was refluxed with stirring for 2 h. After evaporation of the solvent, the resulting oil was crystallized from CH$_2$Cl$_2$/MeOH to give 153 mg (52.3%) of desired compound as HCl salt of white powder.

mp 161.9°–163.5° C.

Anal. Calcd for C$_{22}$H$_{24}$Cl$_2$N$_2$O$_4$.HCl: C, 54.17; H, 5.17; N, 5.74. Found: C, 54.40; H, 5.47; N, 5.62.

$^1$H NMR (270 MHz, CDCl$_3$) δ 11.30 (1H, br.s), 7.45–7.25 (8H, m), 6.45 (1H, m), 4.65–2.00(15H, m).

IR (KBr): 3300, 1740, 1665 cm$^{-1}$.

Example 5

(2S,3S)-1-[2-N-(2-Hydroxyethylamino)-2-phenylethyl]-3-hydroxypyrrolidine

To a stirred suspension of lithium aluminum hydride (380 mg, 10 mmol) in THF (10 ml) was added a solution of (2S, 3S)-1-[2-N-(t-butoxycarbonyl)methylamino-2-phenylethyl]-3-hydroxypyrrolidine (1.602 g, 5 mmol) in THF (15 ml) dropwise at room temperature. The reaction mixture was then refluxed with stirring for 1 h. After cooling down to room temperature, $Na_2SO_4.10H_2O$ (3.80 g) and KF (0.38 g) was added to the reaction mixture. After 1 h stirring, the solid appeared was removed by Celite filtration. The filtrate was concentrated to give 1.32 g (crude 100%) of desired compound as yellow oil.

$^1$H NMR (270 MHz, $CDCl_3$) δ 7.34–7.24 (5H, m), 4.33 (1H, br.s), 3.77 (1H, dd, J=3.7, 11.0Hz), 3.77–3.57 (2H, m), 3.20–3.05 (1H, m), 2.88 (1H, dd, J=11.0, 12.1Hz), 3.05–2.55 (6H, m), 2.35 (1H, dd, J=3.7, 12.1Hz), 2.30–2.15 (2H, m), 1.95–1.75 (2H, m).

IR (neat): 3350 cm$^{-1}$.

Example 6

2-(3,4-Dichlorophenyl)-N-(2-hydroxyethyl)-N-[2-(3-(S)-hydroxypyrrolidin-1-yl)-1-(S)-phenylethyl]acetamide This compound was prepared in 48% yield according to a procedure similar to that described in Example 1.

$^1$H NMR (270 MHz, $CDCl_3$) δ 7.38–7.02 (8H, m), 6.13 (0.75H, br.d, J=9.2Hz), 5.05 (0.25H, m), 4.45–4.35 (1H, m), 4.10–3.10 (9H, m), 2.90–2.15 (6H, m), 1.90–1.75 (1H, m).

IR (neat): 3400, 1640 cm$^{-1}$.

HCl salt: amorphous solid.

Anal. Calcd for $C_{22}H_{26}Cl_2N_2O_3.HCl.2.5H_2O$: C, 50.93; H, 6.22; N, 5.40. Found: C, 51.20; H, 6.02; N, 5.66.

Example 7

(2S,3S)-3-Hydroxy-1-[2-phenyl-2-N-(2,2,2-trifluoroethylamino)ethyl]pyrrolidine

To a stirred solution of (S)-phenylglycyl-3-(S)-hydroxypyrrolidine (1.00 g, 4.5 mmol) in THF (20 ml) was added trifluoroacetic anhydride (0.7 ml, 5 mmol) at room temperature. After 1 h stirring, the solvent was evaporated and the residue was purified by column chromatography (silica gel: 100 g, $CH_2Cl_2$/MeOH:20/1 as eluent) to give 0.90 g of amide derivative, which was dissolved in THF (14 ml) followed by addition of boran-methyl sulfide complex (1.33 ml, 14 mmol) at 0° C. Then the reaction mixture was refluxed for 13 h. To this reaction mixture was added 1N HCl aqueous solution (10 ml) at 0° C. and the mixture was refluxed for 1 h. After cooling down to room temperature, the reaction mixture was basified with 1N NaOH aqueous solution and extracted with $CH_2Cl_2$. After dry ($Na_2SO_4$), the solvent was evaporated to give 0.821 g of colorless oil which was soon crystallized.

$^1$H NMR (270 MHz, $CDCl_3$) δ 7.38–7.20 (5H, m), 4.38–4.30 (1H, m), 3.92 (1H, dd, J=3.3, 11.0Hz), 3.13–2.95 (3H, m), 2.81 (1H, dd, J=11.0, 12.1Hz), 2.85–2.60 (3H, m), 2.38–2.11 (3H, m), 1.95 (1H, br.s), 1.85–1.65 (1H, m).

IR (neat): 3350 cm$^{-1}$.

Example 8

2-(3,4-Dichlorophenyl)-N-[(2-(3-(S)-hydroxypyrrolidin-1-yl)-1-(S)-phenylethyl]-N-(2,2,2-trifluoroethyl)acetamide This compound was prepared in 38.9% yield according to a procedure similar to that described in Example 1.

$^1$H NMR (270 MHz, $CDCl_3$) δ 7.40 (1H, d, J=8.1Hz), 7.36–7.26 (5H, m), 7.16 (1H, br.s), 7.07 (1H, br.d, J=8.1Hz), 5.78 and 5.06 (total 1H, each br.s), 4.27 (1.5H, br.s), 3.90–3.60 (3.5H, m), 3.80–2.80 (3H, m), 2.75–2.60 (2H, m), 2.45–2.05 (2H, m), 1.95–1.60 (2H, m).

IR (neat) 3450, 1660 cm$^{-1}$.

HCl salt: amorphous solid.

Anal. Calcd for $C_{22}H_{23}Cl_2F_3N_2O_2.HCl$: C, 51.63; H, 4.73; N, 5.47. Found: C, 51.78; H, 5.19; N, 5.28.

Example 9

(2S,3S)-1-[2-N-(2-furyl)methylamino-2-phenylethyl]-3-hydroxypyrrolidine

A mixture of (2S,3S)-1-(2-amino-2-phenylethyl)-3-hydroxypyrrolidine (619 mg, 3 mmol), and 2-furaldehyde (0.37 ml, 4.5 mmol) in ethanol (8 ml) was refluxed with stirring for 4.5 h. Then the solvent was evaporated and the resulting Schiff base was dissolved in methanol (10 ml) and to this solution was added $NaBH_4$ by portions at room temperature. After 0.5 h stirring at room temperature, the solvent was evaporated. Then water (30 ml) was added to the residue and extracted with $CH_2Cl_2$. The extract was washed with brine, dried ($MgSO_4$), and concentrated to give 857 mg (99.8%) of brown oil.

$^1$H NMR (270 MHz, $CDCl_3$) δ 7.40–7.28 (6H, m), 6.30 (1H, dd, J=1.8, 2.9Hz), 6.08 (1H, d, J=2.9Hz), 4.33–4.25 (1H, m), 3.75 (1H, d, J=14.7Hz), 3.71 (1H, dd, J=3.7, 11.4Hz), 3.49 (1H, d, J=14.7Hz), 2.84 (1H, dd, J=11.4, 12.1Hz), 2.83–2.75 (1H, m), 2.62–2.51 (2H, m), 2.35 (2H, br.s), 2.27 (1H, dd, J=3.7, 12.1Hz), 2.21–2.10 (2H, m), 1.80–1.65 (1H, m).

IR (neat): 3300 cm$^{-1}$.

Example 10

2-(3,4-Dichlorophenyl)-N-furfuryl-N-[2-(3-(S)-hydroxypyrrolidin-1-yl)-1-(S)-phenylethyl]acetamide This compound was prepared in 96.5% yield according to a procedure similar to that described in Example 1.

$^1$H NMR (270 MHz, $CDCl_3$) δ 7.37 (1H, d, J=8.1Hz), 7.37 (1H, d, J=1.8Hz), 7.31–7.22 (5H, m), 7.10 (1H, dd, J=1.8, 8.1Hz), 7.03 (1H, dd, J=1.8, 8.1Hz), 6.19 (1H, dd, J=1.9, 2.9Hz), 5.94 (1H, dd, J=5.1, 9.5Hz), 5.71 (1H, d, J=2.9Hz), 4.40–4.33 (1H, m), 4.30 (1H, d, J=17.9Hz), 4.22 (1H, d, J=17.9Hz), 3.72 (1H, d, J=13.2Hz), 3.66 (1H, d, J=13.2Hz), 3.59 (1H, dd, J=9.5, 12.8Hz), 3.49 (1H, s), 3.45–3.35 (1H, m), 3.20–3.05 (2H, m), 2.83 (1H, dd, J=5.1, 11.0Hz), 2.65–2.55 (1H, m), 2.55–2.10 (1H, m), 1.95–1.80 (1H, m).

IR (neat): 3400, 1650 cm$^{-1}$.

HCl salt: mp 181.0°–183.5° C.

Anal. Calcd for $C_{25}H_{26}Cl_2N_2O_3$: C, 58.89; H, 5.34; N, 5.49. Found: C, 58.58; H, 5.61; N, 5.63.

Example 11

(2S,3S)-1-[2-Phenylethyl-2-N-(2-thienyl)methylamino]-3-hydroxypyrrolidine

This compound was prepared in 100% yield according to a procedure similar to that described in Example 9.

$^1$H NMR (270 MHz, $CDCl_3$) δ 7.42–7.24 (5H, m), 7.20 (1H, dd, J=1.1, 5.1Hz), 6.94 (1H, dd, J=3.3, 5.1Hz), 6.83 (1H, br.d, J=2.9Hz), 4.30–4.20 (1H, m), 3.90 (1H, d, J=14.3Hz), 3.79 (1H, dd, J=3.7, 11.0Hz), 3.73 (1H, d, J=14.3Hz), 2.84 (1H, dd, J=11.0, 12.1Hz), 2.88–2.77 (1H, m), 2.62–2.52 (2H, m), 2.29 (1H, dd, J=3.7, 12.1Hz), 2.32–2.10 (4H, m), 1.77–1.64 (1H, m).

IR (neat): 3300 cm$^{-1}$.

Example 12

2-(3,4-Dichlorophenyl)-N-[2-(3-(S)-hydroxypyrrolidin-1-yl)-1-(S)-phenylethyl]-N-(2-thienyl)methylacetamide This compound was prepared in 62.6% yield according to a procedure similar to that described in Example 1.

$^1$H NMR (270 MHz, $CDCl_3$) δ 7.39 (1H, d, J=2.2Hz), 7.33 (1H, d, J=8.8Hz), 7.30–7.26 (3H, m), 7.15–7.09 (3H, m), 6.94 (1H, dd, J=2.2, 8.4Hz), 6.83 (1H, dd, J=3.7, 5.1Hz), 6.61 (1H, br.d, J=2.9Hz), 5.99 (1H, dd, J=5.1, 9.5Hz), 4.59 (1H, d, J=17.9Hz), 4.47 (1H, d, J=17.6Hz), 4.43–4.35 (1H, m), 3.67–3.35 (5H, m), 3.21–3.08 (2H, m), 2.87 (1H, dd, J=5.1, 11.0Hz), 2.68–2.56 (1H, m), 2.26–2.14 (1H, m), 1.96–1.85 (1H, m).

IR (neat): 3400, 1650 cm$^{-1}$.

HCl salt: mp 180.7°–184.0° C.

Anal. Calcd for $C_{25}H_{26}Cl_2N_2O_2S \cdot HCl \cdot 0.4H_2O$: C, 56.32; H, 5.26; N, 5.25. Found: C, 56.67; H, 5.38; N, 4.77.

Example 13

(2S,3S)-1-[2-Phenylethyl-2-N-(3-pyridyl)methylamino]-3-hydroxypyrrolidine

This compound was prepared in 63.9% yield according to a procedure similar to that described in Example 9.

$^1$H NMR (270 MHz, CDCl$_3$) δ 8.49 (1H, s), 8.48 (1H, d, J=4.8Hz), 7.63 (1H, dd, J=1.5, 7.7Hz), 7.42–7.27 (5H, m), 7.24 (1H, dd, J=4.8, 7.7Hz), 4.35–4.25 (1H, m), 3.74 (1H, dd, J=3.7, 11.0Hz), 3.73 (1H, d, J=13.8Hz), 3.55 (1H, d, J=13.6Hz), 2.85 (1H, dd, J=11.0, 12.1Hz), 2.88–2.82 (1H, m), 2.60 (2H, d, J=4.0Hz), 2.42 (2H, br.s), 2.31 (1H, dd, J=3.7, 12.1Hz), 2.27–2.09 (2H, m), 1.80–1.65 (1H, m).

IR (neat): 3300 cm$^{-1}$.

Example 14

2-(3,4-Dichlorophenyl)-N-[2-(3-(S)-hydroxypyrrolidin-1-yl)-1-(S)-phenylethyl]-N-(3-pyridyl)methylacetamide This compound was prepared in 56.7% yield according to a procedure similar to that described in Example 1.

$^1$H NMR (270 MHz, CDCl$_3$) δ 8.51 (0.7H, s), 8.48 (0.7H, d, J=4.4Hz), 8.40 (0.3H, d, J=2.9Hz), 8.26 (0.3H, s), 7.55–6.99 (10H, m), 6.26 (0.7H, dd, J=4.0, 11.0Hz), 5.17 (0.3H, t), 4.70 (0.3H, d), 4.41–4.20 (2.7H, m), 3.90 (0.6H, s), 3.58 (0.7H, d), 3.50 (0.7H, d), 3.25–2.35 (5H, m), 2.28–1.95 (2H, m), 1.85–1.60 (2H, m).

IR (neat): 3300, 1650 cm$^{-1}$.

Anal. Calcd for $C_{26}H_{27}Cl_2N_3O_2 \cdot 2HCl \cdot 1.5H_2O$: C, 53.44; H, 5.52; N, 7.19. Found: C, 53.17; H, 5.21; N, 6.91.

Example 15

(2S,3S)-1-[2-Phenylethyl-2-N-(2-pyridyl)methylamino]-3-hydroxypyrrolidine

This compound was prepared in 37.9% yield according to a procedure similar to that described in Example 9.

$^1$H NMR (270 MHz, CDCl$_3$) δ 8.56 (1H, br.d, J=4.8Hz), 7.61 (1H, dt, J=1.8, 7.7Hz), 7.42–7.13 (7H, m), 4.33–4.25 (1H, m), 3.83 (1H, d, J=14.3Hz), 3.73 (1H, dd, J=3.7, 10.6Hz), 3.67 (1H, d, J=14.3Hz), 3.00–2.80 (3H, m), 2.92 (1H, dd, J=10.6, 12.1Hz), 2.70 (1H, br.d, J=9.5Hz), 2.59 (1H, dd, J=4.4, 9.9Hz), 2.36 (1H, dd, J=3.7, 12.1Hz), 2.25–2.09 (2H, m), 1.85–1.70 (1H, m).

IR (neat): 3300 cm$^{-1}$.

Example 16

2-(3,4-Dichlorophenyl)-N-[2-(3-(S)-hydroxypyrrolidin-1-yl)-1-(S)-phenylethyl]-N-(2-pyridyl)methylacetamide This compound was prepared in 68.5% yield according to a procedure similar to that described in Example 1.

$^1$H NMR (270 MHz, CDCl$_3$) δ 8.79 (1H, br.s), 7.66–7.60 (1H, m), 7.33 (1H, d, J=8.4Hz), 7.33–7.23 (6H, m), 7.18 (1H, d, J=1.8Hz), 7.05 (1H, br.d, J=7.7Hz), 6.97 (1H, dd, J=1.8Hz, 8.1Hz), 6.50 (1H, dd, J 3.7, 12.1Hz), 4.70–4.55 (2H, m), 4.37 (1H, d, J=18.3Hz), 4.20 (1H, dd, J=12.5, 12.8Hz), 3.95–3.25 (8H, m), 2.50–2.30 (1H, m), 2.25–2.10 (1H, m).

IR (neat): 3400, 1650 cm$^{-1}$.

HCl Salt: mp 126.5°–132.0° C.

Anal. Calcd for $C_{26}H_{27}Cl_2N_3O_2 \cdot 2HCl \cdot 2H_2O$: C, 52.63; H, 5.61; N, 7.08 Found: C, 52.31; H, 5.39; N, 6.75.

Example 17

(2S,3S)-1-[2-Phenylethyl-2-N-(4-pyridyl)methylamino]-3-hydroxypyrrolidine

This compound was prepared in 81.8% yield according to a procedure similar to that described in Example 9.

$^1$H NMR (270 MHz, CDCl$_3$) δ 8.52 (2H, d, J=5.5Hz), 7.40–7.25 (5H, m), 7.22 (2H, d, J=5.5,Hz), 4.37–4.27 (1H, m), 3.72 (1H, d, J=14.3Hz), 3.75–3.70 (1H, m), 3.56 (1H, d, J=14.7Hz), 2.86 (1H, t, J=11.4Hz), 2.90–2.82 (1H, m), 2.62 (2H, app d), 2.39 (2H, br.s), 2.35–2.10 (3H, m), 1.85–1.68 (1H, m).

IR (neat): 3300 cm$^{-1}$.

Example 18

2-(3,4-Dichlorophenyl)-N-[2-(3-(s)-hydroxypyrrolidin-1-yl)-1-(s)-phenylethyl]-N-(4-pyridyl)methylacetamide This compound was prepared in 10.9% yield according to a procedure similar to that described in Example 1.

$^1$H NMR (270 MHz, CDCl$_3$) δ 8.48 (1.4H, d, J=5.9Hz), 8.40 (0.6H, d, J=5.9Hz), 7.44–6.97 (10H, m), 6.26 (0.7H, dd, J=4.4, 11.0Hz), 5.17 (0.3H, app t), 4.62 (0.3H, d, J=16.1Hz), 4.40–4.30 (1H, m), 4.29 (1.4H, s), 4.26 (0.3H, d, J=16.9Hz), 3.92 (0.6H, s), 3.49 (0.7H, d, J=15.4Hz), 3.41 (0.7H, d, J=15.4Hz), 3.20–2.45 (5H, m), 2.35–2.00 (2H, m), 1.92 (1H, br.s), 1.85–1.65 (1H, m).

IR (neat): 3400, 1650 cm$^{-1}$.

HCl salt: mp 161.1–164.2

Anal. Calcd for $C_{26}H_{27}Cl_2N_3O_2 \cdot 2HCl \cdot 3H_2O$: C, 51.08; H, 5.77; N, 6.87. Found: C, 50.75; H, 5.26; N, 6.83.

Example 19

(2S,3S)-1-[2-N-(4-Methoxycarbonylphenyl)methylamino-2-phenylethyl]-3-hydroxypyrrolidine This compound was prepared in 81.3% yield according to a procedure similar to that described in Example 9.

$^1$H NMR (270 MHz, CDCl$_3$) δ 7.99 (2H, d, J=8.1Hz), 7.40–7.29 (7H, m), 4.35–4.25 (1H, m), 3.91 (3H, s), 3.79 (1H, d, J=13.9Hz), 3.70 (1H, dd, J=3.3, 10.6Hz), 3.57 (1H, d, J=13.9Hz), 2.85 (1H, dd, J=10.6, 12.1Hz), 2.85–2.81 (1H, m), 2.62–2.52 (2H, m), 2.30 (1H, dd, J=3.3, 12.1Hz), 2.27–2.00 (4H, m), 1.80–1.65 (1H, m).

IR (neat): 3280, 3200, 1720 cm$^{-1}$.

Example 20

2-(3,4-Dichlorophenyl)-N-[2-(3-(S)-hydroxypyrrolidin-1-yl)-1-(S)-phenylethyl]-N-(4-methoxycarbonylphenyl)methylacetamide This compound was prepared in 78.5% yield according to a procedure similar to that described in Example 1.

$^1$H NMR (270 MHz, CDCl$_3$) δ 7.83 (2H, d, J=8.1Hz), 7.39–6.90 (10H, m), 6.30–6.15 (1H, m), 4.60–4.10 (3H, m), 3.90 (3H, s), 3.68 (1H, t, J=11.7Hz), 3.63–3.45 (2H, m), 3.30–3.17 (2H, m), 3.10–2.95 (2H, m), 2.74 (1H, br.s), 2.35–2.20 (1H, m), 2.05–1.90 (1H, m).

IR (neat): 3400, 1720, 1650 cm$^{-1}$.

HCl salt: amorphous solid

Anal. Calcd for $C_{29}H_{31}Cl_2N_2O_4 \cdot HCl \cdot 0.7H_2O$: C, 58.88; H, 5.69; N, 4.74. Found: C, 58.56; H, 5.24; N, 4.65.

Example 21

(2S,3S)-1-(2-N-Cyanomethylamino-2-phenylethyl)-3-hydroxypyrrolidine

To a stirred solution of sodium bisulfite (1.249 g, 12 mmol) in water (1 ml) was added 37% aqueous solution of formaldehyde (0.9 ml, 12 mmol) at 0 and the mixture was stirred at room temperature for 0.5 h. Then to this mixture was added (2S,3S)-1-(2-phenylethyl)-3-hydroxypyrrolidine (2.48 g, 12 mmol) and the resulting mixture was stirred at 50 for 0.5 h. After cooling down to room temperature, aqueous solution of KCN (781.4 mg, 12 mmol) was added to the reaction mixture and stirring was continued for 2 h. The reaction mixture was diluted with water (30 ml), extracted with $CH_2Cl_2$ (20 ml×3). The extract was washed with saturated $NaHCO_3$ aqueous solution and dried ($Na_2SO_4$). The solvent was evaporated to give 2.20 g of yellow oil, which was purified by column chromatography (silica gel; 70 g, $CH_2Cl_2$/MeOH: 50/1 as eluent) to afford 1.725 g (58.6%) of colorless viscous oil which was gradually crystallized.

$^1$H NMR (270 MHz, $CDCl_3$) δ 7.39–7.27 (5H, m), 4.40–4.35 (1H, m), 3.96 (1H, dd, J=3.3, 11.4Hz), 3.67 (1H, d, J=17.6Hz), 3.24 (1H, d, J=17.6Hz), 3.17–3.09 (1H, m), 2.87 (1H, app t, J=11.7Hz), 2.75 (1H, dd, J=4.8, 9.9Hz), 2.67 (1H, br.d, J=8.4Hz), 2.36 (1H, dd, J=3.3, 12.1Hz), 2.31–2.10 (3H, m), 1.90 (1H, br.s), 1.88–1.75 (1H, m).

IR (neat) 3300, 2230 $cm^{-1}$.

Example 22
N-Cyanomethyl-2-(3,4-dichlorophenyl)-N-[2-(3-(S)-hydroxypyrrolidin-1-yl)-1-(S)-phenylethyl]acetamide This compound was prepared in 46.6% yield according to a procedure similar to that described in Example 1.

$^1$H NMR (270 MHz, $CDCl_3$) δ 7.38–7.00 (8H, m), 6.09 (0.7H, br.s), 5.31 (0.3H, br.s), 5.09 (1H, br.s), 4.45 (1H, Br.d, J=16.9Hz), 4.40–4.25 (1H, m), 4.15–3.70 (4H, m, including 1H, br.d, J=16.1Hz at 3.95 ppm), 3.65–2.55 (4H, m), 2.50–1.70 (4H, m).

$^{13}$C NMR ($CDCl_3$) d 171.2, 137.4, 134.0, 132.7, 131.4, 131.1, 130.6, 129.3, 128.6, 127.3, 126.3, 116.7, 71.2, 63.2, 59.9, 57.9, 51.9, 39.4, 35.0, 31.0.

IR (neat): 3450, 2250, 1660 $cm^{-1}$.

MS m/e (%): 432 (<4), 189 (22), 161 (93), 159 (100), 145 (39), 143 (35), 132 (32), 125 (31), 123 (37), 117 (30), 100 (99).

Preparation 4
3-(S)-Methoxymethoxypyrrolidine

To a stirred solution of N-benzyl-3-(S)-hydroxypyrrolidine (4.785 g, 27 mmol) in THF (50 ml) was added sodium hydride (60% oil suspension, 1.12 g, 28 mmol) by portions under nitrogen at room temperature. The suspension mixture was then refluxed for 1 h. To this reaction mixture was added chloromethyl methyl ether (2.3 ml, 30 mmol) and refluxing was continued for 13 h. After cooling down to room temperature, water (10 ml) was added to the reaction mixture to give a solution mixture, which was basified with 1N NaOH aqueous solution, extracted with ethyl acetate (30 ml×3), and dried ($Na_2SO_4$). Evaporation of the solvent gave 6.33 g of brown oil, which was purified by column chromatography (silica gel: 150 g, $CH_2Cl_2$/MeOH: 20/1 as eluent) to afford 5.09 g (85%) of clear brown oil. A suspension mixture of this oil (5.09 g, 23 mmol) and Pearlman's catalyst (2.00 g) in MeOH (100 ml) was stirred under hydrogen atmosphere at room temperature for 15 h. After removal of the catalyst by Celite filtration, the filtrate was concentrated to give an oil and water mixture, which was dried in vacuo to afford 2.76 g (91.4%) of orange color oil.

$^1$H NMR (270 MHz, $CDCl_3$) δ 4.65 (1H, d J=7.0Hz), 4.63 (1H, d, J=6.6Hz), 4.30–4.24 (1H, m), 3.37 (3H, s), 3.21 (1H, br.s), 3.17–2.86 (4H, m), 1.98–1.80 (2H,m).

IR (neat): 3300 $cm^{-1}$.

Preparation 5
(S)-Phenylglycyl-3-(S)-methoxymethoxypyrrolidine

This compound was prepared in 61.8% yield using 3-(S)-methoxymethoxypyrrolidine and N-benzyloxycarbonyl-(S)-phenylglycine according to a procedure similar to that described in Preparation 1.

$^1$H NMR (270 MHz, $CDCl_3$) δ 7.36–7.29 (5H, m), 4.66 and 4.63, and 4.46 and 4.35 (total 2H, each d, J=7.0Hz), 4.56 and 4.50 (total 1H, each br.s), 4.27–4.20 (1H, m), 3.81–3.14 (4H, m), 3.36 and 3.10 (total 3H, each s), 2.10–1.80 (2H, m), 2.00 (2H, br.s).

IR (neat): 3350, 3300, 1650 $cm^{-1}$.

Preparation 6
(2S,3S)-1-(2-Amino-2-phenylethyl)-3-(methoxymethoxy)pyrrolidine

This compound was prepared in 97.7% yield according to a procedure similar to that described in Preparation 2.

$^1$H NMR (270 MHz, $CDCl_3$) δ 7.39–7.24 (5H, m), 4.66 (1H, d, J=6.6Hz), 4.63 (1H, d, J=7.0Hz), 4.30–4.23 (1H, m), 4.08 (1H, dd, J=3.3, 10.3Hz), 3.37 (3H, s), 3.00–2.80 (2H, m), 2.74 (1H, dd J=10.3, 11.7Hz), 2.60–2.45 (2H, m), 2.41 (1H, dd, J=3.3, 11.7Hz), 2.21–2.04 (1H, m), 1.95–1.75 (3H, m).

IR (neat): 3400 $cm^{-1}$.

Example 23
(2S,3S)-1-[2-N-(2,2-Difluoroethylamino)-2-phenylethyl]-3-hydroxypyrrolidine To a stirred solution of (2S,3S)-1-(2-amino-2-phenylethyl)-3-(methoxymethoxy)pyrrolidine (0.77 g, 3.08 mmol) and 2,2-difluoroacetic acid (0.21 ml, 3.3 mmol) was added 1-ethyl-3-(3-dimethylaminopropyl)carbodiimide hydrochloride (0.63 g, 3.3 mmol) at room temperature. After 4 h stirring, the reaction mixture was diluted with $CH_2Cl_2$ (20 ml), washed with saturated $NaHCO_3$ aqueous solution and brine, dried ($Na_2SO_4$), and concentrated to give 1.05 g of brown viscous oil. This was purified by column chromatography (silica gel: 100 g, $CH_2Cl_2$/MeOH: 40/1 as eluent) to give 0.69 g (68.3%) of brown viscous oil.

$^1$H NMR (270 MHz, $CDCl_3$) δ 7.37–7.25 (5H, m), 5.91 (1H, t, $J_{H,F}$=54.2Hz), 4.95–4.85 (1H, m), 4.63 (1H, d, J=6.6Hz), 4.59 (1H, d, J=6.6Hz), 4.26–4.19 (1H, m), 3.35 (3H, s), 2.96–2.69 (4H, m), 2.56–2.43 (2H, m), 2.18–2.03 (1H, m), 1.87–1.75 (1H, m), 1.72 (1H, br.s).

IR (neat): 3300, 1700 $cm^{-1}$.

To a stirred solution of this amide derivative (0.69 g, 2.1 mmol) in THF (6 ml) was added $BH_3.Me_2S$ (0.6 ml, 6.3 mmol) at room temperature and then refluxed for 5 h. After cooling down to room temperature, 1N HCl (10 ml) was added dropwise carefully and the resulting mixture was refluxed for 2 h. After cooling down to room temperature, the reaction mixture was basified with 1N NaOH aqueous solution to pH 12 and extracted with $CH_2Cl_2$ (20 ml×3). The extract was dried ($Na_2SO_4$) and concentrated to give 566 mg (67.9% for two steps) of titled compound as yellow viscous oil.

$^1$H NMR (270 MHz, $CDCl_3$) δ 7.37–7.23 (5H, m), 5.76 (1H, ddt, J=3.3, 5.1, 56.1Hz), 4.40–4.25 (1H, m), 3.80 (1H, dd, J=3.7, 10.6Hz), 3.77–3.70 (1H, m), 2.99 (1H, dt, J=5.5, 8.8Hz), 2.95–2.45 (4H, m), 2.82 (1H, dd, J=11.0, 12.1Hz), 2.36–1.95 (3H, m), 1.90–1.70 (2H, m).

IR (neat): 3400, 3330 $cm^{-1}$.

Example 24
2-(3,4-Dichlorophenyl)-N-(2,2-difluoroethyl)-N-[2-(3-(S)-hydroxypyrrolidin-1-yl)-1-(S)-phenylethyl]acetamide This compound was prepared in 62.7% yield according to a procedure similar to that described in Example 1.

¹H NMR (270 MHz, CDCl₃) δ 7.43–7.26 (6H, m), 7.15–7.09 (2H, m), 6.13 (0.5H, dd, J=5.5, 11.0Hz), 6.03 (0.5H, ddt, J=2.9, 5.1, 55.0Hz), 5.27 (0.5H, ddt, J=4.4, 4.8, 56.4Hz), 5.05 (0.5H, dd, J=6.6, 7.7Hz), 4.35–4.25 (1H, m), 3.86 (1H, s), 3.84 (0.5H, d, J=15.8Hz), 3.75 (0.5H, d, J=15.8Hz), 3.70–2.60 (7H, m), 1.80–1.65 (1H, m).

IR (neat): 3450, 1650 cm⁻¹.

HCl salt: amorphous solid

Anal. Calcd for C₂₂H₂₄Cl₂F₂N₂O₂·HCl·H₂O: C, 51.63; H, 5.32; N, 5.47. Found: C, 51.94; H, 5.40; N, 5.51.

Preparation 7
(2S,3S)-1-[2-N-(2-Fluoroethylamino)-2-phenylethyl]-3-(methoxymethoxy)pyrrolidine A mixture of (2S,3S)-1-(2-amino-2-phenylethyl)-3-(methoxymethoxy)pyrrolidine (1.01 g, 4 mmol), 2-bromofluoroethane (0.90 ml, 12 mmol), and K₂CO₃ (0.69 g, 5 mmol) in DMF (5 ml) was stirred at 70 for 13 h. The reaction mixture was diluted with water (10 ml), basified with 1N NaOH aqueous solution to pH12, and extracted with CH₂Cl₂ (30 ml×3). The extract was dried (Na₂SO₄) and concentrated in vacuo to give 1.00 g of dark brown viscous oil, which was purified by column chromatography (silica gel: 100 g, CH₂Cl₂/MeOH: 30/1 as eluent) to afford 0.51 g (43%) of brown viscous oil.

¹H NMR (270 MHz, CDCl₃) δ 7.38–7.25 (5H, m), 4.66 (1H, d, J=7.0Hz), 4.63 (1H, d, J=7.0Hz), 4.60–4.22 (3H, m), 3.77 (1H, dd, J=3.3, 10.3Hz), 3.38 (3H, s), 2.98 (1H, dd, J=6.2, 10.3Hz), 2.94–2.49 (6H, m), 2.34 (1H, dd, J=3.7, 12.1Hz), 2.20–2.06 (1H, m), 1.90–1.78 (1H, m), 1.56 (1H, br.s).

IR (neat): 3320 cm⁻¹.

Example 25
2-(3,4-Dichlorophenyl)-N-(2-fluoroethyl)-N-[2-(3-(S)-hydroxypyrrolidin-1-yl)-1-(S)-phenylethyl]acetamide To a stirred solution of (2S,3S)-1-[2-N-(2-fluoroethylamino)-2-phenylethyl]-3-(methoxymethoxy)pyrrolidine (0.7 g, 2.6 mmol) and triethylamine (0.56 ml, 4 mmol) in CH₂Cl₂ (10 ml) was added 3,4-dichlorophenylacetyl chloride [this was prepared from 3,4-dichlorophenylacetic acid (0.82 g, 4 mmol) and thionyl chloride (0.36 ml, 5 mmol)] at room temperature. After 20 min, the reaction mixture was diluted with CH₂Cl₂ (20 ml), washed with saturated NaHCO₃ aqueous solution and dried (Na₂SO₄). Evaporation of the solvent gave 1.96 g of brown oil, which was purified by column chromatography (silica gel 100 g, CH₂Cl₂/MeOH: 20/1 as eluent) to give 0.81 g (64.3%) of yellow viscous oil. To this oil was added HCl gas saturated MeOH solution (10 ml) and stirred at room temperature for 2 h. The solvent was evaporated and the residue was basified with 1N NaOH aqueous solution to pH 11 and extracted with CH₂Cl₂ (20 ml×2). After dry (Na₂SO₄), the solvent was evaporated to afford 0.78 g of brown viscous oil, which was purified by column chromatography (silica gel: 100 g, CH₂Cl₂/MeOH: 40/1 as eluent) to give 0.598 g (81.5%) of clear yellow viscous oil.

¹H NMR (270 MHz, CDCl₃) δ 7.41–7.26 (6H, m), 7.20–7.09 (2H, m), 6.10 (0.6H, dd, J=5.9, 10.6Hz), 5.03 (0.4H, t, J=7.3Hz), 4.70–3.90 (3H, m), 3.83 (0.6H, d, J=15.4Hz), 3.83 (0.8H, s), 3.75 (0.6H, d, J=15.8Hz), 3.72–3.25 (2H, m), 3.22–2.98 (2H, m), 2.94–2.80 (1H, m), 2.75–2.08 (5H, m), 1.80–1.65 (1H, m).

IR (neat): 3400, 1640 cm⁻¹.

HCl salt: amorphous solid.

Anal. Calcd for C₂₂H₂₅Cl₂FN₂O₂·HCl·2H₂O: C, 51.63; H, 5.91; N, 5.47. Found: C, 51.95; H, 5.64; N, 5.42.

Example 26
(2S,3S)-1-(2-N-Benzylamino-2-phenylethyl)-3-hydroxypyrrolidine

This compound was prepared in 100% yield according to a procedure similar to that described in Example 9.

¹H NMR (270 MHz, CDCl₃) δ 7.43–7.22 (10H, m), 4.30–4.25 (1H, m), 3.77 (1H, d, J=13.6Hz), 3.73 (1H, dd, J=3.7, 11.0Hz), 3.49 (1H, d, J=13.6Hz), 2.87 (1H, dd, J=11.0, 12.1Hz), 2.85–2.75 (1H, m), 2.64–2.51 (2H, m), 2.38 (2H, br.s), 2.30 (1H, dd, J=3.7, 12.1Hz), 2.23–2.07 (2H, m), 1.77–1.65 (1H, m).

IR (neat): 3300 cm⁻¹.

Example 27
N-Benzyl-2-(3,4-Dichlorophenyl)-N-[2-(3-(S)-hydroxypyrrolidin-1-yl)-1-(S)-phenylethyl]acetamide This compound was prepared in 62.6% yield according to a procedure similar to that described in Example 1.

¹H NMR (270 MHz, CDCl₃) δ 7.40–6.78 (13H, m), 6.27 (1H, br.d, J=8.1Hz), 4.93 (1H, br.d, J=17.6Hz), 4.65–4.50 (2H, m), 4.20–3.95 (2H, m), 3.85–3.60 (3H, m), 3.55–3.15 (4H, m), 2.50–2.35 (1H, m), 2.30–2.10 (1H, m).

IR (KBr): 3330, 1640 cm⁻¹.

HCl salt: amorphous solid

Anal. Calcd for C₂₇H₂₈Cl₂N₂O₂·HCl·H₂O: C, 60.29; H, 5.81; N, 5.21. Found: C, 60.49; H, 5.38; N, 5.24.

Example 28
N-Carbamoylmethyl-2-(3,4-Dichlorophenyl)-N-[2-(3-(S)-hydroxypyrrolidin-1-yl)-1-(S)-phenylethyl]acetamide A mixture of N-cyanomethyl-2-(3,4-Dichlorophenyl)-N-[2-(3-(S)-hydroxy-pyrrolidin-1-yl)-1-(S)-phenylethyl]acetamide (2.54 g, 5.9 mmol) and HCl gas saturated methaol (20 ml) was stirred at room temperature for 0.5 h. The reaction mixture was concentrated, basified with aqueous NH₃ solution, and extracted with CH₂Cl₂ (30 ml×3). After dry (Na₂SO₄), the solvent was evaporated to give brown biscous oil, which was purified by column chromatography (silica gel: 100 g, CH₂Cl₂/MeOH: 30/1 to 15/1 as eluent) to afford 1.25 g (47.3%) of pale yellow viscous oil.

¹H NMR (270 MHz, CDCl₃) δ 10.14 (1H, br.s), 7.40–7.09 (8H, m), 6.31 (1H, dd, J=3.3, 12.8Hz), 5.70 (1H, br.s), 4.42 (1H, m), 3.80–3.55 (4H, m), 3.50–3.40 (1H, m), 3.35 (1H, app t, J=12.8Hz), 2.76 (1H, J=10.3Hz), 2.75–2.64 (2H, m, including 1H, dd, J=3.3, 12.8Hz at 2.67 ppm), 2.30–2.15 (2H, m), 1.90–1.70 (2H, m).

¹³C NMR (CDCl₃) δ 173.2, 172.1, 137.4, 134.5, 132.5, 131.1, 130.4, 128.94, 128.86, 128.6, 128.3, 127.1, 70.4, 63.1, 53.9, 53.4, 51.4, 47.7, 39.8, 34.7.

IR (KBr): 3400, 1690, 1650 cm⁻¹.

MS m/e (%): 450 (3), 431 (2), 429 (3), 408 (2), 406 (3), 363 (4), 243 (3), 189 (75), 163 (99), 161 (94), 159 (99), 132 (36), 125 (55), 118 (100), 104 (95), 101 (98), 91 (91), 89 (70), 82 (61).

HCl salt: amorphous solid

Anal. Calcd for C₂₂H₂₅Cl₂N₃O₃·HCl·H₂O: C, 52.34; H, 5.59; N, 8.32. Found: C, 52.41; H, 5.38; N, 7.96.

Example 29
(2S,3S)-3-Hydroxy-1-[2-N-(2-methoxyethylamino)-2-phenylethyl]pyrrolidine To a stirred solution of (2S,3S)-1-(2-amino-2-phenylethyl)-3-hydroxypyrrolidine (0.619 g, 3 mmol) and 2-methoxyacetic acid (0.23 ml, 3 mmol) in CH₂Cl₂ (10 ml) was added 1-ethyl-3-(3-dimethylaminopropyl)carbodiimide hydrochloride (0.863 g, 4.5 mmol) at room temperature. After 0.5 h stirring, the reaction mixture was diluted with water (50 ml) and extracted with $CH_2Cl_2$ (30 ml×3). The extract was washed with saturated $NaHCO_3$ aqueous solution and brine, dried ($Na_2SO_4$), and concentrated to give 0.711 g of clear yellow viscous oil. This was purified by column chromatography (silica gel:40 g, $CH_2Cl_2$/MeOH: 30/1 as eluent) to give 0.44 g (52.7%) of pale yellow viscous oil.

$^1$H NMR (270 MHz, $CDCl_3$) δ 7.35–7.22 (6H, m), 5.07–4.99 (1H, m), 4.30–4.20 (1H, m), 3.91 (2H, s), 3.42 (3H, s), 3.02 (1H, s), 2.94–2.85 (2H, m), 2.67 (1H, dd, J=5.1, 12.5Hz), 2.60 (2H, d, J=4.4Hz), 2.36–2.27 (1H, m), 2.17–2.07 (1H, m), 1.71–1.66 (1H, m).

IR (neat): 3350, 3270, 1660 $cm^{-1}$.

To a stirred suspension of lithium aluminum hydride (0.24 g, 6 mmol) in THF (10 ml) was added a solution of this amide derivative (0.44 g, 1.58 mmol) in THF (20 ml) dropwise at room temperature and then the mixture was refluxed for 3.5 h. After cooling down to room temperature, $Na_2SO_4$ 10$H_2O$ (2.00 g) and KF (0.2 g) was added to the reaction mixture. After 20 min stirring, the solid appeared was removed by Celite filtration. The filtrate was concentrated and the residue was purified by column chromatography (silica gel: 12 g, $CH_2Cl_2$/MeOH: 30/1 as eluent) to give 0.118 g (28.2%) of pale yellow viscous oil.

$^1$H NMR (270 MHz, $CDCl_3$) δ 7.39–7.23 (5H, m), 4.35–4.26 (1H, m), 3.78 (1H, dd, J=3.7, 10.6Hz), 3.53–3.40 (2H, m), 3.35 (3H, s), 3.10–3.00 (1H, m), 2.95–2.85 (3H, m), 2.87–2.60 (4H, m), 2.38 (1H, dd, J=3.9, 12.1Hz), 2.33–2.15 (2H, m), 1.85–1.73 (1H, m).

IR (neat): 3400, 3330 $cm^{-1}$.

Example 30

2-(3,4-Dichlorophenyl)-N-[2-(3-(S)-hydroxypyrrolidin-1-yl)-1-(S)-phenylethyl]-N-(2-methoxyethyl)acetamide This compound was prepared in 77.2% yield according to a procedure similar to that described in Example 1.

$^1$H NMR (270 MHz, $CDCl_3$) δ 7.40–7.25 (6H, m), 7.18–7.05 (2H, m), 5.93 (0.8H, dd, J=5.9, 9.9Hz), 5.00 (0.2H, t), 4.35–4.25 (1H, m), 3.82 (1H, d, J=15.4Hz), 3.75 (1H, d, J=15.4Hz), 3.55–2.55 (13H, m, including 2.4H, s, at 3.19 ppm), 2.50–2.35 (1H, m), 2.25–2.10 (1H, m), 1.85–1.70 (1H, m).

IR (neat): 3400, 1640 $cm^{-1}$.

HCl salt: amorphous solid.

Anal. Calcd for $C_{23}H_{28}Cl_2N_2O_3$ HCl 2.2$H_2O$: C, 52.37; H, 6.38; N, 5.31. Found: C, 52.29; H, 6.40; N, 5.32.

Example 31

(2S,3S)-3-Hydroxy-1-[2-N-(2-methylthioethylamino)-2-phenylethyl]pyrrolidine

This compound was prepared in 50.5% yield according to a procedure similar to that described in Example 29.

$^1$H NMR (270 MHz, $CDCl_3$) δ 7.38–7.24 (5H, m), 4.35–4.26 (1H, m), 3.75 (1H, dd, J=3.7, 10.6Hz), 3.10–3.00 (1H, m), 2.85 (1H, dd, J=10.6, 12.1Hz), 2.75–2.55 (5H, m), 2.41–2.15 (6H, m, including 1H, dd, J=4.0, 12.1Hz at 2.38 ppm), 2.05 (3H, s), 1.85–1.70 (1H, m).

IR (neat): 3300 $cm^{-1}$.

Example 32

2-(3,4-Dichlorophenyl)-N-[2-(3-(S)-hydroxypyrrolidin-1-yl)-1-(S)-phenylethyl]-N-(2-methylthioethyl)acetamide This compound was prepared in 64.8% yield according to a procedure similar to that described in Example 1.

$^1$H NMR (270 MHz, $CDCl_3$) δ 7.45–7.25 (6H, m), 7.18–7.10 (2H, m), 6.06 (0.6H, dd, J=5.9, 10.3Hz), 5.02 (0.4H, dd, J=6.2, 8.4Hz), 4.38–4.25 (1H, m), 3.83 (0.8H, s), 3.76 (0.6H, d, J=15.4Hz), 3.68 (0.6H, d, J=15.4Hz), 3.50–1.65 (16H, m, including 1.2H, s, at 1.99 ppm and 1.8H, s, at 1.96 ppm), 2.50–2.35 (1H, m), 2.25–2.10 (1H, m), 1.85–1.70 (1H, m).

IR (neat): 3450, 1640 $cm^{-1}$.

HCl salt: mp 195°–197.5° C.

Anal. Calcd for $C_{23}H_{28}Cl_2N_2O_2S$ HCl 0.5$H_2O$: C, 53.86; H, 5.90; N, 5.46. Found: C, 54.08; H, 5.91; N, 5.39.

Example 33

(2S,3S)-1-[2-N-(2-N,N-Dimethylaminoethylamino)-2-phenylethyl]-3-metoxymetoxypyrrolidine This compound was prepared in 53.1% yield according to a procedure similar to that described in Example 29.

$^1$H NMR (270 MHz, $CDCl_3$) δ 7.39–7.20 (5H, m), 4.65 (1H, d, J=7.0Hz), 4.62 (1H, d, J=6.6Hz), 4.28–4.21 (1H, m), 3.70 (1H, dd, J=3.7, 10.6Hz), 3.37 (3H, s), 2.95 (1H, dd, J=6.2, 9.9Hz), 2.82 (1H, dd, J=10.6, 11.7Hz), 2.80–2.71 (1H, m), 2.59–2.45 (4H, m), 2.42–2.30 (4H, m), 2.18 (6H, s), 2.16–2.05 (1H, m), 1.85–1.75 (1H, m).

IR (neat): 3300 $cm^{-1}$.

Example 34

2-(3,4-Dichlorophenyl)-N-(2-N,N-dimethylaminoethylamino)-N-[2-(3-(S)-hydroxypyrrolidin-1-yl)-1-(S)-phenylethyl]acetamide This compound was prepared in 88% yield according to a procedure similar to that described in Examples 1 and 25.

$^1$H NMR (270 MHz, $CDCl_3$) δ 7.41–7.08 (8H, m), 6.03 (0.7H, dd, J=5.9, 9.9Hz), 5.01 (0.3H, dd, J=7.0, 7.3Hz), 4.32–4.22 (1H, m), 3.79 (0.6H, s), 3.77 (0.7H, d, J=15.4Hz), 3.70 (0.7H, d, J=15.4Hz), 3.36 (0.6H, app.t, J=7.0Hz), 3.20 (1.4H, app.t, J=7.3Hz), 3.15–3.00 (2H, m), 2.95–2.80 (1H, m), 2.75–2.50 (2H, m), 2.50–1.61 (6H, m), 2.11 (1.8H, s), 2.09 (4.2H, s).

IR (neat): 3400, 1640 $cm^{-1}$.

HCl salt: amorphous solid.

Anal. Calcd for $C_{24}H_{31}Cl_2N_3O_2$ 2HCl 1.3$H_2O$: C, 51.40; H, 6.40; N, 7.49. Found: C, 51.79; H, 7.01; N, 7.58.

Example 35

(2S,3S)-1-[2-N-(2,2-Dimethoxyethylamino)-2-phenylethyl]-3-hydroxypyrrolidine

This compound was prepared in 66% yield according to a procedure similar to that described in Example 2.

$^1$H NMR (270 MHz, $CDCl_3$) δ 7.38–7.22 (5H, m), 4.45 (1H, t, J=5.1Hz), 4.33–4.27 (1H, m), 3.74 (1H, dd, J=3.7, 10.6Hz), 3.36 (3H, s), 3.30 (3H, s), 3.08–3.00 (1H, m), 2.85 (1H, dd, J=10.6, 12.1Hz), 2.71 (1H, br.d, J=9.5Hz), 2.65–2.55 (3H, m, including 2H, d, J=5.1Hz at 2.61 ppm), 2.37 (1H, dd, J=3.7, 12.1Hz), 2.32–2.12 (4H, m), 1.81–1.72 (1H, m).

IR (neat): 3400, 3300 $cm^{-1}$.

Example 36

2-(3,4-Dichlorophenyl)-N-(2,2-dimethoxyethyl)-N-[2-(3-(S)-hydroxypyrrolidin-1-yl)-1-(S)-phenylethyl]acetamide This compound was prepared in 91.2% yield according to a procedure similar to that described in Example 1.

$^1$H NMR (270 MHz, $CDCl_3$) δ 7.41–7.10 (8H, m), 6.09 (1H, dd, J=5.9, 9.9Hz), 4.35–4.25 (1H, m), 3.94 (1H, d, J=15.4Hz), 3.85 (1H, d, J=15.8Hz), 3.59 (1H, t, J=5.1Hz), 3.34–3.15 (3H, m), 3.22 (3H, s), 3.18 (3H, s), 3.10–3.00 (1H, m), 2.86 (1H, dd, J=5.9,12.5Hz), 2.76–2.63 (2H, m), 2.40–2.25 (1H, m), 2.20–2.08 (1H, m), 1.90–1.65 (2H, m).

IR (neat): 3450, 1640 $cm^{-1}$.

Fumalic acid salt: amorphous solid.

Anal. Calcd for $C_{24}H_{30}Cl_2N_2O_4 \cdot C_4H_4O_4 \cdot 2H_2O$: C, 53.09; H, 6.05; N, 4.92. Found: C, 53.47; H, 6.04; N, 4.51.

Example 37
(2S,3S)-3-Hydroxy-1-[2-phenylethyl-2-N-(2-pyrrolyl) methyl-amino]pyrrolidine This compound was prepared in 100% yield according to a procedure similar to that described in Example 9.

$^1$H NMR (270 MHz, CDCl$_3$) δ 9.29 (1H, br.s), 7.37–7.25 (5H, m), 6.75 (1H, d, J=1.5Hz), 6.12 (1H, dd, J=2.6, 5.5Hz), 5.97 (1H, br.s), 4.35–4.25 (1H, m), 3.78 (1H, d, J=13.9Hz), 3.73 (1H, dd, J=3.3, 11.3Hz), 3.55 (1H, d, J=13.9Hz), 3.31 (2H, br.s), 2.92 (1H, dd, J=11.7, 12.1Hz), 2.87–2.77 (2H, m), 2.52 (1H, dd, J=4.8, 9.9Hz), 2.30 (1H, dd, J=3.3, 12.1Hz), 2.25–2.02 (2H, m), 1.83–1.73 (1H, m).

IR (neat): 3300 cm$^{-1}$.

Example 38
2-(3,4-Dichlorophenyl)-N-[2-(3-(S)-hydroxypyrrolidin-1-yl)-1-(S)-phenylethyl]-N-(2-pyrrolyl)methylacetamide This compound was prepared in 81.3% yield according to a procedure similar to that described in Example 1.

$^1$H NMR (270 MHz, CDCl$_3$) δ 12.00 (1H, br.s), 7.45–7.25 (6H, m), 7.08 (1H, d, J=1.5Hz), 6.87 (1H, dd, J=1.5, 8.1Hz), 6.80–6.75 (1H, m), 6.38 (1H, dd, J=3.7, 12.8Hz), 6.13 (1H, dd, J=2.6, 5.1Hz), 5.99 (1H, br.s), 4.58–4.50 (1H, m), 4.15 (2H, s), 3.65–3.40 (4H, m), 3.00–2.90 (2H, m), 2.80–2.65 (2H, m), 2.40–2.25 (2H, m), 1.90–1.65 (2H, m).

IR (neat): 3450, 1630 cm$^{-1}$.

Fumalic acid salt: amorphous solid.

Anal. Calcd for $C_{25}H_{27}Cl_2N_3O_2 \cdot C_4H_4O_4 \cdot H_2O$: C, 57.43; H, 5.48; N, 6.93. Found: C, 57.46; H, 5.41; N, 6.95.

Example 39
(2S,3S)-3-Hydroxy-1-[2-N-(1-methyl-2-pyrrolyl) methylamino-2-phenylethyl]pyrrolidine This compound was prepared in 100% yield according to a procedure similar to that described in Example 9.

$^1$H NMR (270 MHz, CDCl$_3$) δ 7.43–7.24 (5H, m), 6.55 (1H, dd, J=1.8, 2.6Hz), 6.05–5.99 (2H, m), 4.30–4.25 (1H, m), 3.75 (1H, dd, J=3.7, 10.6Hz), 3.61 (1H, d, J=13.9Hz), 3.55 (3H, s), 3.49 (1H, d, J=13.6Hz), 2.87–2.81 (1H, m), 2.81 (1H, dd, J=10.6, 12.1Hz), 2.62–2.53 (2H, m), 2.29 (1H, dd, J=3.7, 12.1Hz), 2.27–2.08 (2H, m), 1.99 (2H, br.s), 1.76–1.65 (1H, m).

IR (neat): 3250 cm$^{-1}$.

Example 40
2-(3,4-Dichlorophenyl)-N-[2-(3-(S)-hydroxypyrrolidin-1-yl)-1-(S)-phenylethyl]-N-(1-methyl-2-pyrrolyl)methylacetamide This compound was prepared in 57.6% yield according to a procedure similar to that described in Example 1.

$^1$H NMR (270 MHz, DMSO-d$_6$) δ 7.54 (1H, d, J=8.1Hz), 7.39 (1H, br.s ), 7.35–7.20 (5H, m), 7.17 (1H, br.d, J=8.4Hz), 6.59 (1H, br.s), 5.85–5.70 (2H, m), 5.60–5.50 (1H, m), 4.75–4.60 (1H, m), 4.42 (2H, ABq), 4.13 (1H, br.s), 3.70 (1H, s), 3.41 (3H, s), 3.10–2.75 (3H, m), 2.65–2.20 (4H, m), 2.00–1.85 (1H, m), 1.55–1.45 (1H, m).

IR (neat): 3450, 1640 cm$^{-1}$.

Fumalic acid salt: amorphous solid.

Anal. Calcd for $C_{25}H_{27}Cl_2N_3O_2 \cdot C_4H_4O_4 \cdot 1.5H_2O$: C, 57.24; H, 5.76; N, 6.67. Found: C, 57.17; H, 5.40; N, 6.52.

Example 41
(2S,3S)-3-Hydroxy-1-[2-N-(methoxylcarbonyl) methylamino-2-phenylethyl]pyrrolidine This compound was prepared in 81.4% yield according to a procedure similar to that described in Preparation 3.

$^1$H NMR (270 MHz, CDCl$_3$) δ 7.36–7.24 (5H, m), 4.37–4.30 (1H, m), 3.82 (1H, dd, J=3.7, 11.0Hz), 3.69 (3H, s), 3.39 (1H, d, J=17.9Hz), 3.22–3.15 (1H, m), 3.18 (1H, d, J=17.6Hz), 2.86 (1H, dd, J=11.0, 12.1Hz), 2.73 (1H, dd, 4.8, 9.9Hz), 2.66 (1H, br.d, J=8.1Hz), 2.60–2.15 (5H, m, including 1H, dd, J=3.7, 12.1Hz, at 2.32 ppm), 1.82–1.75 (1H, m).

Example 42
2-(3,4-Dichlorophenyl)-N-[2-(3-(S)-hydroxypyrrolidin-1-yl)-1-(S)-phenylethyl]-N-methoxycarbonylmethylacetamide This compound was prepared in 57.6% yield according to a procedure similar to that described in Example 1.

$^1$H NMR (270 MHz, CDCl$_3$) δ 7.41–7.20 (6H, m), 7.16–7.08 (2H, m), 6.03 (0.5H, dd, J=5.9, 10.3Hz), 4.99 (0.5H, dd, J=6.2, 8.8Hz), 4.28 (0.5H, d, J=16.9Hz), 4.30–4.20 (1H, m), 3.90 (1H, s), 3.87 (0.5H, d, J=16.9Hz), 3.77 (0.5H, d, J=12.5Hz), 3.75 (1H, s), 3.72 (0.5H, d, J=12.5Hz), 3.68 (1.5H, s), 3.63 (1.5H, s), 3.16–2.42 (5H, m), 2.27–1.65 (4H, m).

IR (neat): 3450, 1750, 1650 cm$^{-1}$.

HCl salt: mp 169°–172° C.

Anal. Calcd for $C_{23}H_{26}Cl_2N_2O_4 \cdot HCl \cdot 0.5H_2O$: C, 54.08; H, 5.52; N, 5.48. Found: C, 54.39; H, 5.49; N, 5.53.

Example 43
(2S,3S)-1-[2-N-(2-Cyanoethylamino)-2-phenylethyl]-3-hydroxypyrrolidine A mixture of (2S,3S)-1-(2-amino-2-phenylethyl)-3-hydroxypyrrolidine (0.619 g, 3 mmol) and acrylonitrile (1 ml, 15 mmol) in ethanol (6 ml) was stirred at room temperature for 13 h. The solvent was evaporated to give 0.786 mg (100%) of a yellow solid.

$^1$H NMR (270 MHz, CDCl$_3$) δ 7.39–7.24 (5H, m), 4.37–4.32 (1H, m), 3.76 (1H, dd, J=3.7, 11.0Hz), 3.08–3.00 (1H, m), 2.90–2.72 (3H, m, including 1H, dd, J=11.0, 12.1Hz, at2.82 ppm), 2.69 (2H, d, J=3.7Hz), 2.53–2.14 (7H, m, including 1H, dd, J=3.7, 12.1Hz at 2.34 ppm), 1.83–1.73 (1H, m).

IR (neat): 3350, 3280, 2250 cm$^{-1}$.

Example 44
N-2-Cyanoethyl-2-(3,4-dichlorophenyl)-N-[2-(3-(S)-hydroxypyrrolidin-1-yl)-1-(S)-phenylethyl]acetamide This compound was prepared in 93.3% yield according to a procedure similar to that described in Example 29.

$^1$H NMR (270 MHz, CDCl$_3$) δ 7.42–7.06 (8H, m), 6.11 (0.3H, dd, J=4.8, 11.4Hz), 5.03 (0.7H, dd, J=5.9, 9.2Hz), 4.40–4.28 (1H, m), 3.85–3.40 (4H, m, including 2H, br.s at 3.77 ppm), 3.30–2.60 (5H, m), 2.45–2.08(4H, m), 1.90 (1H, br.s), 1.80–1.65 (1H, m).

IR (neat): 3450, 2250, 1650 cm$^{-1}$.

Maleic acid salt: amorphous solid.

Anal. Calcd for $C_{23}H_{25}Cl_2N_3O_2 \cdot C_4H_4O_4 \cdot H_2O$: C, 55.87; H, 5.38; N, 7.24. Found: C, 56.12; H, 5.35 N, 7.26.

Example 45
2-(Benzo[b]furan-4-yl)-N-[2-(3-(S)-hydroxypyrrolidin-1-yl)-1-(S)-phenylethyl]-N-methoxycarbonylmethylacetamide This was prepared in 83.7% yield according to a procedure similar to that described in Example 1.

$^1$H NMR (270 MHz, CDCl$_3$, it appeared as 1:1 rotamer mixture by amide bond) δ 7.64 (0.5H, d, J=2.2Hz), 7.61

(0.5H, d, J=2.2Hz), 7.46–7.40 (1H, m), 7.35–7.20 (6.5H, m), 7.10–7.05 (1.5H, m), 6.88 (0.5H, d, J=2.2Hz), 6.85 (0.5H, d, J=2.2Hz), 6.09 (0.5H, dd, J=5.9, 10.6Hz), 5.09 (0.5H, dd, J=7.3, 8.1Hz), 4.26 (0.5H, d, J=16.5Hz), 4.24–4.10 (1H, m), 4.07–3.84 (3H, m, including 1H, s, at 4.02 ppm and 1H, s, at 3.92 ppm), 3.81 (0.5H, d, J=16.5Hz), 3.65 (1.5H, s), 3.61 (1.5H, s), 3.18–3.09 (1H, m), 2.95–1.55 (8H, m).

IR (KBr): 3420, 1740, 1635 $cm^{-1}$.

Fumalic acid salt: amorphous solid.

Anal. Calcd for $C_{25}H_{28}N_2O_5 \cdot C_4H_4O_4 \cdot 0.5H_2O$: C, 62.02; H, 5.92; N, 4.99. Found: C, 62.08; H, 5.80; N, 4.97.

Example 46

N-[2-(3-(S)-Hydroxypyrrolidin-1-yl)-1-(S)-phenylethyl]-N-methoxycarbonylmethyl-2-(4-trifluoromethylphenyl) acetamide This was prepared in 87.9% yield according to a procedure similar to that described in Example 1.

$^1$H NMR (270 MHz, $CDCl_3$, it appeared as 1:1 rotamer mixture by amide bond) δ 7.60 (1H, d, J=8.4Hz), 7.57 (1H, d, J=8.8Hz), 7.43 (1H, d, J=8.1Hz), 7.37 (1H, d, J=8.1Hz), 7.34–7.26 (4H, m), 7.10 (1H, d, J=2.2, 7.7Hz), 6.05 (0.5H, dd, J=5.9, 10.6Hz), 5.00 (0.5H, dd, J=7.0, 8.1Hz), 4.25 (0.5H, d, J=16.8Hz), 4.30–4.15 (1H, m), 3.95–3.73 (3.5H, m), 3.67 (1.5H, s), 3.62 (1.5H, s), 3.20–3.05 (1H, m), 3.00–1.55 (8H, m).

IR (neat): 3450, 1750, 1650 $cm^{-1}$.

Fumalic acid salt: amorphous solid.

Anal. Calcd for $C_{24}H_{27}F_3N_2O_4 \cdot C_4H_4O_4 \cdot 0.5H_2O$: C, 57.04; H, 5.47; N, 4.75. Found: C, 57.23; H, 5.31; N, 4.70.

Example 47

N-[2-(3-(S)-Hydroxypyrrolidin-1-yl)-1-(S)-phenylethyl]-N-methoxycarbonylmethyl-2-(3-nitrophenyl)acetamide This was prepared in 97.8% yield according to a procedure similar to that described in Example 1.

$^1$H NMR (270 MHz, $CDCl_3$, it appeared as 1:1 rotamer mixture by amide bond) δ 8.13–8.06 (2H, m), 7.64 (1H, br.d, J=7.0Hz), 7.50 (1H, dd, J=7.7, 8.8Hz), 7.40–7.15 (5H, m), 6.05 (0.5H, dd, J=5.9, 10.6Hz), 5.06 (0.5H, dd, J=6.2, 8.8Hz), 4.29 (0.5H, d, J=16.8Hz), 4.30–4.20 (1H, m), 3.97 (1H, s), 3.97–3.87 (2H, m, including 1H, dd, J=4.0, 9.5Hz at 3.92 ppm), 3.78 (0.5H, d, J=15.7Hz), 3.68 (1.5H, s), 3.66 (1.5H, s), 3.20–2.46 (5H, m), 2.32–1.65 (4H, m).

IR (neat): 3450, 1750, 1650 $cm^{-1}$.

Fumalic acid salt: mp 78°–80.5°.

Anal. Calcd for $C_{23}H_{27}N_3O_6 \cdot C_4H_4O_4 \cdot H_2O$: C, 56.34; H, 5.78; N, 7.30. Found: C, 56.62; H, 5.83; N, 7.07.

Example 48

2-(3-Bromophenyl)-N-[2-(3-(S)-hydroxypyrrolidin-1-yl)-1-(S)-phenylethyl]-N-methoxycarbonylmethylacetamide This was prepared in 82.7% yield according to a procedure similar to that described in Example 1.

$^1$H NMR (270 MHz, $CDCl_3$, it appeared as 1:1 rotamer mixture by amide bond) δ 7.48–7.10 (9H, m), 6.05 (0.5H, dd, J=5.9, 10.6Hz), 4.97 (0.5H, dd, J=6.6, 8.4Hz), 4.30 (0.5H, d, J=16.9Hz), 4.27–4.15 (1H, m), 3.89 (1H, s), 3.86 (0.5H, d, J=18.3Hz), 3.80–3.72 (2H, m), 3.69 (1.5H, s), 3.62 (1.5H, s), 3.16–2.52 (4.5H, m), 2.39 (0.5H, dd, J=4.8, 9.5Hz), 2.25–2.00 (2.5H, m), 1.80–1.60 (1.5H, m).

IR (neat): 3450, 1750, 1650 $cm^{-1}$.

Fumalic acid salt: amorphous solid.

Anal. Calcd for $C_{23}H_{27}BrN_2O_4 \cdot C_4H_4O_4 \cdot H_2O$: C, 53.21; H, 5.46; N, 4.60. Found: C, 53.43; H, 5.26; N, 4.36.

Example 49

N-[2-(3-(S)-Hydroxypyrrolidin-1-yl)-1-(S)-phenylethyl]-N-methoxycarbonylmethyl-2-(2,3,6-trichlorophenyl) acetamide This was prepared in 67.2% yield according to a procedure similar to that described in Example 1.

$^1$H NMR (270 MHz, $CDCl_3$, it appeared as 3:2 rotamer mixture by amide bond) δ 7.45–7.25 (7H, m), 6.04 (0.6H, dd, J=5.9, 10.3Hz), 5.24 (0.4H, dd, J=5.5, 8.8Hz), 4.35–3.80 (5H, m), 3.68 (1.8H, s), 3.63 (1.2H, s), 3.21–3.02 (2H, m), 2.85–2.05 (5H, m), 1.90–1.60 (2H, m).

IR (neat): 3450, 1740, 1660 $cm^{-1}$.

Fumalic acid salt: amorphous solid.

Anal. Calcd for $C_{23}H_{25}Cl_3N_2O_4 \cdot C_4H_4O_4 \cdot H_2O$: C, 51.16; H, 4.93; N, 4.42. Found: C, 51.38; H, 4.96; N, 4.29.

Example 50

N-[2-(3-(S)-Hydroxypyrrolidin-1-yl)-1-(S)-phenylethyl]-N-methoxycarbonylmethyl-2-(1-napththyl)acetamide This was prepared in 70.2% yield according to a procedure similar to that described in Example 1.

$^1$H NMR (270 MHz, $CDCl_3$, it appeared as 1:1 rotamer mixture by amide bond) δ 7.98 (0.5H, d, J=7.7Hz), 7.90–7.75 (2.5H, m), 7.65–7.15 (9H, m), 6.14 (0.5H, dd, J=5.5, 10.6Hz), 5.06 (0.5H, dd, J=6.6, 8.4Hz), 4.40–4.13 (3.5H, m), 3.95 (1H, s), 3.88 (0.5H, d, J=16.9Hz), 3.67 (1.5H, s), 3.62 (1.5H, s), 3.25–1.95 (7.5H, m), 1.80–1.60 (1.5H, m).

IR (KBr): 3500, 1740, 1630 $cm^{-1}$.

Fumalic acid salt: mp 189.5°–193.5°.

Anal. Calcd for $C_{27}H_{30}N_2O_4 \cdot C_4H_4O_4 \cdot 0.5H_2O$: C, 65.14; H, 6.17; N, 4.90. Found: C, 65.35; H, 6.04; N, 4.91.

Example 51

(2S,3S)-1-[2-N-(1,2,4-Oxadiazol-3-yl)methylamino-2-phenylethyl]-3-hydroxypyrrolidine A mixture of 2-(3-(S)-hydroxypyrrolidin-1-yl)-1-(S)-phenylethylamine (0.619 g, 3 mmol), 3-chloromethyl-1,2,4-oxadiazole (533 mg, 4.5 mmol), and $K_2CO_3$ (415 g, 3 mmol) in DMF (4 ml) was stirred at room temperature for 16 h. The reaction mixture was poured into water (30 ml) and extracted with ethyl acetate (20 ml×3). The extract was washed with brine, dried ($Na_2SO_4$), and concentrated to give 982 mg of a yellow oil, which was purified by column chromatography (silica gel; 40 g, $CH_2Cl_2$/MeOH: 40/1 to 10/1) to afford 347 mg (40.1%) of title compound.

$^1$H NMR (270 MHz, $CDCl_3$) δ 8.69 (1H, s), 7.40–7.25 (5H, m), 4.33–4.28 (1H, m), 3.93 (1H, d, J=15.4Hz), 3.79 (1H, d, J=15.4Hz), 3.80–3.75 (1H, m), 3.00–2.86 (2H, m), 2.70–2.60 (2H, m), 2.40–2.31 (3H, m), 2.29–2.10 (2H, m), 1.79–1.70 (1H, m).

Example 52

2-(3,4-Dichlorophenyl)-N-[2-3-(S)-hydroxypyrrolidin-1-yl)-1-(S)-phenylethyl]-N-(1,2,4-oxadiazol-3-yl) methylacetamide This was prepared in 84.4% yield according to a procedure similar to that described in Example 1.

$^1$H NMR (270 MHz, $CDCl_3$, it appeared as 4:1 rotamer mixture by amide bond) δ 8.66 (0.8H, s), 8.60 (0.2H, s), 7.50–7.14 (8H, m), 6.15 (0.8H, dd, J=5.5, 11.0Hz), 5.11 (0.2H, t, J=6.2Hz), 4.90 (0.2H, d, J=16.1Hz), 4.48 (0.2H, d, J=16.1Hz), 4.41 (1.6H, s), 4.25–3.85 (3H, m), 3.27 (0.8H, dd, J=11.7, 12.5Hz), 3.20–1.65 (8.2H, m).

IR (neat): 3450, 1730, 1650 $cm^{-1}$.

Fumalic acid salt: amorphous solid.
Anal. Calcd for $C_{23}H_{24}C_{12}N_4O_3 \cdot C_4H_4O_4 \cdot H_2O$: C, 53.21; H, 4.96; N, 9.19. Found: C, 53.37; H, 4.87; N, 9.12.

Example 53

2-(Benzo[b]furan-4-yl)-N-[2-(3-(S)-hydroxypyrrolidin-1-yl)-1-(S)-phenylethyl]-N-(1,2,4-oxadiazol-3-yl)methylacetamide This was prepared in 61.1% yield according to a procedure similar to that described in Example 1.

$^1$H NMR (270 MHz, CDCl$_3$, it appeared as 3:1 rotamer mixture by amide bond) δ 8.66 (0.75H, s), 8.59 (0.25H, s), 7.62 (1H, d, J=2.2Hz), 7.43 (1H, d, J=8.1Hz), 7.35–7.05 (7H, m), 6.94 (0.75H, d, J=1.1Hz), 6.87 (0.25H, d, J=1.1Hz), 6.19 (0.75H, dd, J=5.5, 11.0Hz), 5.20 (0.25H, d, J=6.2, 8.8Hz), 4.91 (0.25H, d, J=16.1Hz), 4.48 (0.75H, d, J=17.2Hz), 4.41 (0.25H, d, J=16.1Hz), 4.37 (0.75H, d, J=17.2Hz), 4.33 (1.5H, s), 4.20–4.10 (1.5H, m, including 0.5H, s, at 4.11 ppm), 3.30 (0.75H, dd, J=11.7, 12.1Hz), 3.20–1.55 (8.25H, m, including 0.75H, dd, J=5.5, 12.5Hz at 2.68 ppm).

IR (neat): 3450, 1740, 1650 cm$^{-1}$.

Fumalic acid salt: amorphous solid.

Anal. Calcd for $C_{25}H_{26}N_4O_4 \cdot C_4H_4O_4 \cdot H_2O$: C, 59.99; H, 5.56; N, 9.65. Found: C, 59.74; H, 5.26; N, 9.40.

Example 54

(2S,3S)-1-[2-N-(N',N'-Dimethylaminocarbonyl)methylamino-2-phenylethyl]-3-hydroxypyrrolidine A mixture of (2S,3S)-1-(2-amino-2-phenylethyl)-3-hydroxypyrrolidine (0.413 g, 2 mmol), 2-chloro-N,N-dimethylacetamide (292 mg, 2.4 mmol), and K$_2$CO$_3$ (276 mg, 2 mmol) in DMF (4 ml) was stirred at 50° for 2.5 h. The reaction mixture was poured into water (10 ml) and extracted with ethyl acetate (20 ml×3). After dry (Na$_2$SO$_4$), the solvent was evaporated to give 558 mg of brown oil, which was purified by column chromatography (silica gel: 20 g, CH$_2$Cl$_2$/MeOH: 30/1 to 10/1) to give 94.4 mg (33.4%) of yellow oil.

$^1$H NMR (270 MHz, CDCl$_3$) δ 7.45–7.20 (5H, m), 4.40–4.25 (1H, m), 3.82 (1H, br.d, J=8.4Hz), 3.36 (1H, d, J=16.5Hz), 3.25–3.10 (2H, m, including 1H, d, J=16.1Hz, at 3.17 ppm), 3.00–2.05 (17H, m, including 3H, s, at 2.95 ppm), 1.90–1.75 (1H, m).

IR (neat): 3400, 1640 cm$^{-1}$.

Example 55

2-(3,4-Dichlorophenyl)-N-(N',N'-dimethylaminocarbonyl)methyl-N-[2-(3-(S)-hydroxypyrrolidin-1-yl)-1-(S)-phenylethyl]acetamide This was prepared in 64.6% yield according to a procedure similar to that described in Example 1.

$^1$H NMR (270 MHz, CDCl$_3$, it appeared as 3:2 rotamer mixture by amide bond) δ 7.41–7.12 (8H, m), 6.09 (0.6H, dd, J=6.4, 9.2Hz), 5.10 (0.4H, t, J=7.3Hz), 4.37 (0.4H, d, J=15.7Hz), 4.30–4.20 (1H, m), 3.97–3.58 (3.6H, m), 3.30–1.70 (15H, m, including 1.2H, s, at 2.98 ppm, 1.2H, s, at 2.93 ppm, 1.8H, s, at 2.89 ppm, 1.8H, s, at 2.86 ppm).

IR (neat): 3450, 1650 cm$^{-1}$.

Fumalic acid salt: amorphous.

Anal. Calcd for $C_{24}H_{29}C_{12}N_3O_3 \cdot C_4H_4O_4 \cdot 1.2H_2O$: C, 54.59; H, 5.79; N, 6.82. Found: C, 54.81; H, 6.17; N, 6.84.

Example 56

(2S,3S)-3-Hydroxy-1-[2-N-(6-methylpyridin-2-yl)methylamino-2-phenylethyl]pyrrolidine This was prepared in 92.8% yield according to a procedure similar to that described in Example 9.

$^1$H NMR (270 MHz, CDCl$_3$) δ 7.49 (1H, t, J=7.7Hz), 7.45–7.25 (5H, m), 7.01 (1H, d, J=7.7Hz), 6.96 (1H, d, J=7.7Hz), 4.35–4.25 (1H, m), 3.81 (1H, d, J=13.9Hz), 3.70 (1H, dd, J=3.7, 11.0Hz), 3.61 (1H, d, J=14.3Hz), 3.05–2.85 (5H, m, including 1H, dd, J=10.6, 12.1Hz), 2.71 (1H, d, J=9.9Hz), 2.65–2.55 (4H, m, including 3H, s at 2.54 ppm), 2.33 (1H, dd, J=3.7, 12.1Hz,), 2.25–2.10 (2H, m), 1.90–1.70 (1H, m).

IR (neat): 3300 cm$^{-1}$.

Example 57

2-(3,4-Dichlorophenyl)-N-[2-(3-(S)-hydroxypyrrolidin-1-yl)-1-(S)-phenylethyl]-N-(6-methylpyridin-2-yl)methylacetamide This was prepared in 57.6% yield according to a procedure similar to that described in Example 1.

$^1$H NMR (270 MHz, CDCl$_3$, it appeared as 5:1 rotamer mixture by amide bond) δ 7.45–6.90 (11H, m), 6.20 (0.8H, dd, J=5.1, 9.9Hz), 5.20–5.10 0.2H, m), 4.92 (0.2H, d), 4.43 (1.6H, s), 4.40 (0.2H, d), 4.30–4.23 (0.8H, m), 4.20–4.15 (0.2H, m), 4.02 (0.4H, s), 3.66 (0.8H, d, J=15.4Hz), 3.58 (0.8H, d, J=15.4Hz), 3.30–3.08 (2H, m), 2.80–2.65 (2H, m, including 0.8H, dd, J=5.1, 12.5Hz at 2.75 ppm), 2.60–1.55 (8H, m, including 2.4H, s at 2.50 ppm).

IR (neat): 3400, 1650 cm$^{-1}$.

HCl salt: amorphous solid.

Anal. Calcd for $C_{27}H_{29}C_{12}N_3O_2 \cdot 2HCl \cdot 4.4H_2O$: C, 49.84; H, 6.17; N, 6.46. Found: C, 49.58; H, 6.36; N, 6.86.

I claim:

1. A compound of the following formula:

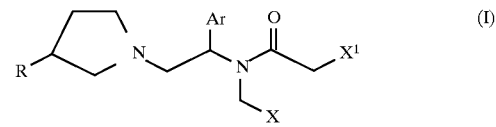

and its pharmaceutically acceptable salt, wherein

R is hydroxy;

Ar is phenyl or phenyl substituted with one to three substituents selected from halo C$_1$–C$_4$alkyl, C$_{1-4}$ alkoxy;

X is phenyl or heterocyclic; phenyl or heterocyclic substituted with one to three substituents selected from halo, C$_{1-4}$ alkyl, C$_{1-4}$ alkoxy and methoxycarbonyl; mono-, di- or tri-halomethyl; cyano; COR$^1$, CH=NOR$^2$, OR$^2$, SR$^2$, CH$_2$CN, CH$_2$OR$^2$, CH$_2$SR$^2$, CH$_2$S(O)R$^2$, CH$_2$S(O)$_2$R$^2$, CH$_2$N(R$^2$)R$^3$, CH$_2$NR$^2$OH, CH$_2$N(COR$^2$)OH, CH$_2$NR$^2$COR$^3$, CH$_2$NR$^2$S(O)$_2$R$^3$ or CH$_2$OCOR$^2$, wherein R$^1$ is hydrogen, hydroxy, amino, NHOH, NHOCH$_3$, pyridylamino, NHN(CH$_3$)$_2$, C$_{1-4}$ alkoxy, benzyloxy, C$_{1-4}$ alkylamino, di-C$_{1-4}$ alkylamino, C$_{1-4}$ alkyl or C$_{1-4}$ alkylthio; and R$^2$ and R$^3$ are each hydrogen, C$_{1-4}$ alkyl, C$_{1-4}$ alkoxy or C$_{7-11}$ phenylalkyl; and X$^1$ is phenyl, naphthyl, furyl, thienyl, pyridyl, thiazolyl, benzofuryl or benzothienyl; phenyl, naphthyl, furyl, thienyl, pyridyl, thiazolyl, benzofuryl or benzothienyl, substituted with one to three substituents selected from halo, C$_{1-4}$ alkyl, C$_{1-4}$ alkoxy, amino, hydroxy, nitro, trifluoromethyl and mesyl.

2. A compound according to claim 1, wherein Ar is phenyl optionally substituted with one to three halogen atoms; and X$^1$ is phenyl optionally substituted with one to three halogen atoms.

3. A compound according to claim 2, wherein Ar is phenyl and X$^1$ is 3,4-dichlorophenyl.

4. A compound according to claim 3, wherein X is phenyl optionally substituted with one to three substituents selected from halo, C$_{1-4}$ alkyl, C$_{1-4}$ alkoxy and methoxycarboxyl.

5. A compound according to claim 3, wherein X is mono-, di- or trihalomethyl, cyano, hydroxycarbonyl, butyloxycarbonyl, benzyloxycarbonyl, carbamoyl or hydroxymethyl.

6. A compound according to claim 3, wherein X is heterocyclic selected from furyl, thienyl, pyridyl and oxadiazolyl.

7. A compound according to claim 1, being one of the following:

N-carboxymethyl-2-(3,4-dichlorophenyl)-N-[2-(3(S)-hydroxypyrrolidin-1-yl)-1-(S)-phenylethyl]acetamide;

2-(3,4-dichlorophenyl)-N-2-hydroxyethyl)-N-[2-(3-(S)-hydroxypyrrolidin-1-yl)-1-(S)-phenylethyl]acetamide;

2-(3,4-dichlorophenyl)-N-[(2-(3-(S)-hydroxypyrrolidin-1-yl)-(S)-phenylethyl]-N-(2,2,2-trifluoroethyl)acetamide;

2-(3,4-dichlorophenyl)-N-furfuryl-N-[2-(3-(S)-hydroxypyrrolidin-1-yl)-1-(S)-phenylethyl]acetamide;

2-(3,4-dichlorophenyl)-N-[2-(3-(S)-hydroxypyrrolidin-1-yl)-1-(S)-phenylethyl]-N-(4-pyridyl)methylacetamide;

2-(3,4-dichlorophenyl)-N-[2-(3-(S)-hydroxypyrrolidin-1-yl)-1-(S)-phenylethyl]-N-(3-pyridyl)methylacetamide;

N-cyanomethyl-2-3(3,4-dichlorophenyl)-N-[2-(3-(S)-hydroxypyrrolidin-1-yl)-1-(S)-phenylethyl]acetamide;

2-(3,4-dichlorophenyl)-N-(2,2-difluoroethyl)-N-[2-(3-(S)-hydroxypyrrolidin-1-yl)-1-(S)-phenylethyl]acetamide;

N-2-cyanoethyl-2-(3,4-dichlorophenyl)-N-[2-(3-(S)-hydroxypyrrolidin-1-yl)-1-(S)-phenylethyl]acetamide;

2-(3,4-dichlorophenyl)-N-[2-(3-(S)-hydroxypyrrolidin-1-yl)-1-(S)-phenylethyl]-N-methoxycarbonylmethylacetamide; and 2-(3,4-dichlorophenyl)-N-[2-(3-(S)-hydroxypyrrolidin-1-yl)-1-(S)-phenylethyl]-N-(1,2,4-oxadiazol-3-yl)methylacetamide.

8. A compound of the formula:

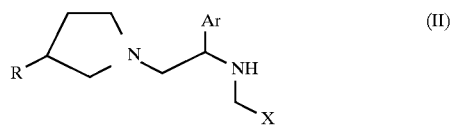

(II)

wherein

R is hydroxy;

Ar is phenyl or phenyl substituted with one to three substituents selected from halo, $C_{1-4}$ alkyl and $C_{1-4}$ alkoxy; and X is phenyl or heterocyclic; phenyl or heterocyclic substituted with one to three substituents selected from halo, $C_{1-4}$ alkyl, $C_{1-4}$ alkoxy and methoxycarbonyl; mono-, di- or tri-halomethyl; cyano; $COR^1$, $CH=NOR^2$, $OR^2$, $SR^2$, $CH_2CN$, $CH_2OR^2$, $CH_2SR^2$, $CH_2S(O)R^2$, $CH_2S(O)_2R^2$, $CH_2N(R^2)R^3$, $CH_2NR^2OH$, $CH_2N(COR^2)OH$, $CH_2NR^2COR^{3'}$ $CH_2NR^2S(O)_2R^3$ or $CH_2OCOR^2$, wherein $R^1$ is hydrogen, hydroxy, amino, NHOH, NHOCH$_3$, pyridylamino, NHN(CH$_3$)$_2$, $C_{1-4}$ alkoxy, benzyloxy, $C_{1-4}$ alkylamino, di-$C_{1-4}$ alkylamino, $C_{1-4}$ alkyl or $C_{1-4}$ alkylthio; and $R^2$ and $R^3$ are each hydrogen, $C_{1-4}$ alkyl, $C_{1-4}$ alkoxy or $C_{7-11}$ phenylalkyl.

9. A compound according to claim 8, wherein Ar is phenyl.

10. A compound according to claim 9, wherein X is phenyl, methoxycarbonylphenyl, mono-, di or tri-halomethyl, cyano, hydroxycarbonyl, butyloxycarbonyl, benzyloxycarbonyl, carbamoyl, hydroxymethyl, furyl, thienyl, pyridyl or oxadiazolyl.

11. A pharmaceutically composition useful as an analgesic, antiinflammatory, diuretic or neuroprotective agent, which comprises a compound according to claim 1, and a pharmaceutically inert carrier.

* * * * *